United States Patent [19]
Perlin

[11] Patent Number: 5,541,067
[45] Date of Patent: * Jul. 30, 1996

[54] METHOD AND SYSTEM FOR GENOTYPING

[76] Inventor: Mark W. Perlin, 5904 Beacon St., Pittsburgh, Pa. 15217

[*] Notice: The portion of the term of this patent subsequent to Jun. 17, 2014, has been disclaimed.

[21] Appl. No.: 314,900

[22] Filed: Sep. 29, 1994

Related U.S. Application Data

[63] Continuation-in-part of Ser. No. 261,169, Jun. 17, 1994.
[51] Int. Cl.$^6$ .............................. C12Q 1/68; C12P 19/34; C07H 21/04
[52] U.S. Cl. .................. 435/6; 435/91.2; 536/24.31; 536/24.33; 204/461; 204/466; 204/612; 204/616; 382/128; 382/129; 382/140
[58] Field of Search ......... 435/91.2, 6; 536/24.3–24.33; 204/182.8; 302/16; 382/128, 129

[56] References Cited

U.S. PATENT DOCUMENTS

| | | | |
|---|---|---|---|
| 5,161,204 | 11/1992 | Hutcheson et al. | 382/16 |
| 5,273,632 | 12/1993 | Stockham et al. | 204/180.1 |

OTHER PUBLICATIONS

Perlin et al. "Toward Fully Automated Genotyping: Genotyping Microsatellite Markers By Deconvolution", Am. J. Hum. Genetics 57:119–21 1995.
Schwartz et al. "Fluorescent mulitplex linkage analysis and carrier detection for Duchenne/Becker Muscular Dystrophy" Am J. Human Genet. 51: 721–729, 1992.

*Primary Examiner*—W. Gary Jones
*Assistant Examiner*—Dianne Rees
*Attorney, Agent, or Firm*—Ansel M. Schwartz

[57] ABSTRACT

The present invention pertains to a process which can be fully automated for accurately determining the alleles of STR genetic markers. More specifically, the present invention is related to performing PCR amplification on locations of DNA, labelling the PCR products, converting the labels into a signal, removing a reproducible PCR stutter pattern from the signal by means of a computational device, and then determining the genotype of the location of the DNA. An amplification can include multiple locations from the DNA of one or more individuals. The invention also pertains to genetics applications and systems which can effectively use this genotyping information.

16 Claims, 10 Drawing Sheets

(STEP 1) ACQUIRE AN INDIVIDUAL'S GENOMIC DNA (STEP 2) PERFORM PCR AMPLIFICATION AT AN STR LOCUS OF THIS DNA (STEP 3) SIZE SEPARATION ASSAY OF THE AMPLIFIED PCR PRODUCTS (STEP 4) ANALYZE THE PEAKS OF THE RESULTING ASSAY INTO DNA SIZE VS. CONCENTRATION FEATURES (STEP 5) DECONVOLVE THE ANALYZED PCR PRODUCT TO DETERMINE THE GENOTYPE OF THE INDIVIDUAL AT THE STR LOCUS (STEP 5') DECONVOLUTION USING FOURIER DOMAIN SIGNAL PROCESSING (STEP 6) EMPLOYING A PCR STUTTER PATTERN LIBRARY

*FIG. 1B*

DATA FROM MARKER STR-45.

| SIZE | INDIVIDUAL A | INDIVIDUAL E |
|---|---|---|
| 161 | 821 | 930 |
| 163 | 2171 | 1928 |
| 165 | 7242 | 5896 |
| 167 | 20799 | 18115 |
| 169 | 55373 | 47391 |
| 171 | 101299 | 94852 |
| 173 | 0 | 61326 |
| 175 | 0 | 0 |

DATA FROM MARKER STR-49.

| SIZE | INDIVIDUAL D |
|---|---|
| 221 | 843 |
| 223 | 1217 |
| 225 | 2360 |
| 227 | 6123 |
| 229 | 11469 |
| 231 | 26811 |
| 233 | 48135 |
| 234 | 0 |
| 236 | 0 |
| 238 | 0 |
| 240 | 0 |
| 242 | 0 |
| 244 | 0 |
| 246 | 0 |
| 248 | 0 |
| 250 | 0 |
| 252 | 1695 |
| 254 | 2877 |
| 256 | 5410 |
| 258 | 11553 |
| 260 | 17482 |
| 262 | 25866 |
| 264 | 28672 |

*FIG. 3A*

USING THE MW MARKERS TO CONSTRUCT THE
DATA EXPECTATIONS

USING THE DATA EXPECTATIONS TO LOCALIZE
AND QUANTITATE DATA (STEP 1) DETERMINE GENOTYPES OF RELATED INDIVIDUALS.

(STEP 2) SET CHROMOSOME PHASE BY GRAPH PROPAGATION, DEDUCTIVE METHODS, OR LIKELIHOOD ANALYSIS.

(STEP 3) DETERMINE THE PHENOTYPIC RISK OF DISEASE FOR THE INDIVIDUALS.

(STEP 4) PRESENT THE RESULTS.

*FIG. 6*

METHOD AND SYSTEM FOR GENOTYPING

The present application is a continuation-in-part of U.S. patent Ser. No. 08/261,169, filed Jun. 17, 1994, pending

FIELD OF THE INVENTION

The present invention pertains to a process which can be fully automated for accurately determining the alleles of STR genetic markers. More specifically, the present invention is related to performing PCR amplification on DNA, assaying the PCR products, and then determining the genotype of the PCR products. The invention also pertains to systems which can effectively use this genotyping information.

BACKGROUND OF THE INVENTION

To study polymorphisms in genomes, reliable allele determination of genetic markers is required for accurate genotyping. A genetic marker corresponds to a relatively unique location on a genome, with normal mammalian individuals having two (possibly identical) alleles 104 for a marker on an autosomal chromosome 102, referring to FIG. 1A. (Though there are other cases of 0, 1, or many alleles that this invention addresses, this characterization suffices for the background introduction.) One important class of markers is the CA-repeat loci. This class is abundantly represented throughout the genomes of many species, including humans.

A CA-repeat marker allele is comprised of a nucleic acid word 106

PQRST, where P is the left PCR primer, T defines the right PCR primer, Q and S are relatively fixed sequences, and the primary variation occurs in the sequence R, which is a tandemly repeated sequence 108 of the dinucleotide CA, i.e., $R=(CA)_n$, where is n is an integer that generally ranges between ten and fifty. Thus, the length of the allele sequence uniquely determines the content of the sequence, since the only polymorphism is in the length of R.

One can therefore obtain genomic DNA, perform PCR amplification of a CA-repeat genetic marker location, and then assay the length of the allele sequences by differential sizing, typically done by differential migration of DNA molecules using gel electrophoresis. The resulting gel 110 should, in principle, clearly show the alleles of marker for each individual's genome. Further, these sizes can be determined quantitatively by reference to molecular weight markers 112.

However, the PCR amplification of a CA-repeat location produces an artifact, often termed "PCR stutter". Most likely due to slippage of the polymerase molecule on the nucleic acid polymer in the highly repetitive CA-repeat region, the result is that PCR products are produced that correspond to deletions of tandem CA molecules in the repeat region. Thus, instead of a single band on a gel corresponding to the one molecule PQ $(CA)_n$ ST, an entire population of different size bands {PQ $(CA)_n$ ST, PQ $(CA)_{n-1}$ ST, PQ $(CA)_{n-2}$ ST, . . . } in varying concentrations is observed. This PCR stuttering 114 can be viewed as a spatial pattern p(x), or, alternatively, as a response function r(t) of an impulse signal corresponding to the assayed allele.

The stutter artifact can be extremely problematic when the two alleles of an autosomal CA-repeat marker are close in size. Then, their two stutter patterns overlap, producing a complex signal 116. In the presence of background measurement noise, this complexity often precludes unambiguous determination of the two alleles. To date, this has prevented reliable automated (or even manual) genotyping of CA-repeat markers from differential sizing assays.

This overlap of stutter patterns can be modeled as a superposition of two corrupted signals. Importantly, (1) the corrupting response function is roughly identical for two closely sized alleles of the same CA-repeat marker, and (2) this response function is largely determined by the specific CA-repeat marker, the PCR conditions, and possibly the relative size of the allele. Thus, the response functions can be assayed separately from the genotyping experiment. By combining 118 the corrupted signal together with the determined response functions of the CA-repeat marker, the true uncorrupted allele sizes can be determined, and reliable genotyping can be performed.

A primary goal of the NIH/DOE Human Genome Project during its initial 5 year phase of operation was to develop a genetic map of humans with markers spaced 2 to 5 cM apart (E. P. Hoffman, "The Human Genome Project: Current and future impact," *Am. J. Hum. Genet.*, vol. 54, pp. 129–136, 1994), incorporated by reference. This task has already been largely accomplished in half the time anticipated, with markers that are far more informative than originally hoped for. In these new genetic maps, restriction fragment length polymorphism (RFLP) loci have been entirely replaced by CA repeat loci (dinucleotide repeats, also termed "microsatellites") (J. Weber and P. May, "Abundant class of human DNA polymorphisms which can be typed using the polymerase chain reaction," *Am J Hum Genet*, vol. 44, pp. 388–396, 1989; J. Weber, "Length Polymorphisms in dC-dA . . . dG-dT Sequences," Marshfield Clinic, Marshfield, Wis., assignee code 354770, U.S. Pat. No. 5,075,217, 1991), incorporated by reference, and other short tandem repeat markers (STRs). It is expected that at least 30,000 CA-repeat markers will be made available in public databases in the form of PCR primer sequences and reaction conditions. One of the advantages of CA repeat loci is their high density in the genome, with about 1 informative CA repeat every 50,000 bp: this permits a theoretical density of approximately 20 loci per centimorgan. Another advantage of CA repeat polymorphisms is their informativeness, with most loci in common use having PIC values of over 0.70 (J. Weissenbach, G. Gyapay, C. Dib, A. Vignal, J. Morissette, P. Millasseau, G. Vaysseix, and M. Lathrop, "A second generation linkage map of the human genome," *Nature*, vol. 359, pp. 794–801, 1992; G. Gyapay, et. al., *Nature Genetics*, vol. 7, pp. 246–239, 1994), incorporated by reference. Finally, these markers are PCR-based, permitting rapid genotyping using minute quantities of input genomic DNA. Taken together, these advantages have facilitated linkage studies by orders of magnitude: a single full-time scientist can cover the entire genome at a 10 cM resolution and map a disease gene in an autosomal dominant disease family in about 1 year (D. A. Stephan, N. R. M. Buist, A. B. Chittenden, K. Ricker, J. Zhou, and E. P. Hoffman, "A rippling muscle disease gene is localized to 1q41: evidence for multiple genes," *Neurology*, in press, 1994), incorporated by reference.

The CA repeat-based genetic maps are not without disadvantages. First, alleles are detected by size differences in PCR products, which often differ by as little as 2 bp in a 300 bp PCR product. Thus, these alleles must be distinguished using high resolution sequencing gels, which are more labor intensive and technically demanding to use than most other electrophoresis systems. Second, referring to FIG. 2, CA repeat loci often show secondary "stutter" or "shadow" bands in addition to the band corresponding to the primary allele, thereby complicating allele interpretation. These stutter bands may be due to errors in Taq polymerase replication during PCR, secondary structure in PCR products, or somatic mosaicism for allele size in a patient. Allele interpretation is further complicated by the differential mobility of the two complementary DNA strands of the PCR products when both are labelled. Finally, sequencing gels often show inconsistencies in mobility of DNA fragments, making it difficult to compare alleles of individuals between gels and often within a single gel. The most common experimental approach used for typing CA repeat alleles involves incorporation of radioactive nucleotide precursors into both strands of the PCR product. The combined consequence of stutter peaks and visualization of both strands of alleles differing by 2 bp often leads to considerable "noise" on the resulting autoradiograph "signals", referring to FIG. 2 which then requires careful subjective interpretation by an experienced scientist in order to determine the true underlying two alleles.

The stuttered signals of di-, tri-, tetra-, and other polynucleotide repeats can be modeled as the convolution of the true allele sizes with a stutter pattern $p(x)$. Under this model, the complex quantitative banding signal $q(x)$ observed on a gel can be understood as the summation of shifted patterns $p(x)$, with one shifted pattern for each allele size. A key fact is that generally only one $p(x)$ function is associated with a given genetic marker, its PCR primers and conditions, and the allele size. In the important case of two alleles, where the two allele sizes are denoted by s and t, one can write the expression $$q(x)=(x^s+x^t)\, p(x).$$

The multiplication of the polynomial expressions $(x^s+x^t)$ and $p(x)$ is one implementation of the underlying (shift and add) convolution process. Given the observed data $q(x)$ and the known stutter pattern $p(x)$, one can therefore determine the unknown allele sizes s and t via a deconvolution procedure. (Note that this convolution/deconvolution model extends to analyses with more than two alleles.)

A corollary of highly dense and informative genetic maps is the need to accurately acquire, analyze and store large volumes of data on each individual or family studied. For example, a genome-wide linkage analysis on a 30 member pedigree at 10 cM resolution would generate data for approximately 30,000 alleles, with many markers showing five or more alleles. Currently, alleles are visually interpreted and then manually entered into spreadsheets for analysis and storage. This approach requires a large amount of time and effort, and introduces the high likelihood of human error. Moreover, future studies of complex multifactorial disease loci will require large-scale genotyping on hundreds or thousands of individuals. Finally, manual genotyping is arduous, boring, time consuming, and highly error prone. Each of these features suggests that automation of genotype data generation, acquisition, interpretation, and storage is required to fully utilize the developing genetic maps. Some effort has been made to assist in allele identification and data storage (ABI Genotyper manual and software, Applied Biosystems Inc.), incorporated by reference. However, this software still requires substantial user interaction to place manually assigned alleles into a spreadsheet, and is unable to deconvolve (hence cannot accurately genotype) closely spaced alleles or perform other needed analyses. Importantly, no essential use is made of a CA-repeat marker's PCR stutter response pattern by the ABI software or by any other disclosed method or system for genotyping.

The Duchenne/Becker muscular dystrophy (DMD/BMD) gene locus (dystrophin gene) (A. P. Monaco, R. L. Neve, C. Colletti-Feener, C. J. Bertelson, D. M. Kurnit, and L. M. Kunkel, "Isolation of candidate cDNAs for portions of the Duchenne muscular dystrophy gene," *Nature*, vol 323, pp 646–650, 1986; M. Koenig, E. P. Hoffman, C. J. Bertelson, A. P. Monaco, C. Feener, and L. M. Kunkel, "Complete cloning of the Duchenne muscular dystrophy cDNA and preliminary genomic organization of the DMD gene in normal and affected individuals," *Cell*, vol 50, pp 509–517, 1987), incorporated by reference, is a useful experimental system for illustrating the automation of genetic analysis. The dystrophin gene can be considered a mini-genome: it is by far the largest gene known to date (2.5 million base pairs); it has a high intragenic recombination rate (10 cM, i.e., 10% recombination between the 5' and 3' ends of the gene); and it has a considerable spontaneous mutation rate ($10^{-4}$ meioses). Mutation of the dystrophin gene results in one of the most common human lethal genetic diseases, and the lack of therapies for DMD demands that molecular diagnostics be optimized. The gene is very well characterized, with both precise genetic maps (C. Oudet, R. Heilig, and J. Mandel, "An informative polymorphism detectable by polymerase chain reaction at the 3' end of the dystrophin gene," *Hum Genet*, vol. 84, pp. 283–285, 1990), incorporated by reference, and physical maps (M. Burmeister, A. Monaco, E. Gillard, G. van Ommen, N. Affara, M. Ferguson-Smith, L. Kunkel, and H. Lehrach, "A 10-megabase physical map of human Xp21, including the Duchenne muscular dystrophy gene," *Genomics*, vol. 2, pp. 189–202, 1988), incorporated by reference. Finally, approximately one dozen CA repeat loci distributed throughout the dystrophin gene have been isolated and characterized (A. Beggs and L. Kunkel, "A polymorphic CACA repeat in the 3' untranslated region of dystrophin," *Nucleic Acids Res*, vol 18, pp. 1931, 1990; C. Oudet, R. Heilig, and J. Mandel, "An informative polymorphism detectable by polymerase chain reaction at the 3' end of the dystrophin gene," *Hum Genet*, vol. 84, pp. 283–285, 1990; P. Clemens, R. Fenwick, J. Chamberlain, R. Gibbs, M. de Andrade, R. Chakraborty, and C. Caskey, "Linkage analysis for Duchenne and Becker muscular dystrophies using dinucleotide repeat polymorphisms," *Am J Hum Genet*, vol 49, pp. 951–960, 1991; C. Feener, F. Boyce, and L. Kunkel, "Rapid detection of CA polymorphisms in cloned DNA: application to the 5' region of the dystrophin gene," *Am J Hum Genet*, vol 48, pp. 621–627, 1991), incorporated by reference.

Many of the problems with interpretation of dystrophin gene CA repeat allele data can be overcome by single or multiplex fluorescent PCR and data acquisition on automated sequencers (L. S. Schwartz, J. Tarleton, B. Popovich, W. K. Seltzer, and E. P. Hoffman, "Fluorescent Multiplex Linkage Analysis and Carrier Detection for Duchenne/ Becker Muscular Dystrophy," *Am. J. Hum. Genet.*, vol. 51, pp. 721–729, 1992), incorporated by reference. This approach uses fluorescently labeled PCR primers to simultaneously amplify four CA repeat loci in a single reaction. By visualizing only a single strand of the PCR product, and by reducing the cycle number, much of the noise associated with these CA repeat loci was eliminated. Moreover, the production of fluorescent multiplex reaction kits provides a standard source of reagents which do not deteriorate for several years following the fluorescent labeling reactions. In this previous report, referring to FIG. 2, alleles were manually interpreted from the automated sequencer traces. Coverage of the entire human genome at 10 cM resolution in fluorescently labeled polynucleotide markers for use in semiautomated genotyping is available (Map Pairs, Research Genetics, Huntsville, Ala.; P. W. Reed, J. L. Davies, J. B. Copeman, S. T. Bennett, S. M. Palmer, L. E. Pritchard, S. C. L. Gough, Y. Kawaguchi, H. J. Cordell, K. M. Balfour, S. C. Jenkins, E. E. Powell, A. Vignal, and J. A. Todd, "Chromosome-specific microsatellite sets for fluorescence-based, semi-automated genome mapping," *Nature Genetics*, in press, 1994), incorporated by reference.

This invention pertains to automating data acquisition and interpretation for any STR genetic marker. In the preferred embodiment, the invention: identifies each of the marker alleles at an STR locus in an organism; deconvolves complex "stuttered" alleles which differ by as few as two bp (i.e., at the limits of signal/noise); makes this genotyping information available for further genetic analysis. For example, to establish DMD diagnosis by linkage analysis in pedigrees, the application system: identifies each of the dystrophin gene alleles in pedigree members; deconvolves complex "stuttered" alleles which differ by only two bp where signal/noise is a particular problem; reconstructs the pedigrees from lane assignment information; sets phase in females; propagates haplotypes through the pedigree; identifies female carriers and affected males in the pedigree based on computer derivation of an at-risk haplotype; detects and localizes recombination events within the pedigree. Other uses of automatically acquired STR genetic marker data are the construction of genetic maps (T. C. Matise, M. W. Perlin, and A. Chakravarti, "Automated construction of genetic linkage maps using an expert system (MultiMap): application to 1268 human microsatellite markers," *Nature Genetics*, vol. 6, no. 4, pp. 384–390, 1994), incorporated by reference, the localization of genetic traits onto chromosomes (J. Ott, *Analysis of Human Genetic Linkage, Revised Edition*. Baltimore, Md.: The Johns Hopkins University Press, 1991), incorporated by reference, and the positional cloning of genes derived from such localizations (B. -S. Kerem, J. M. Rommens, J. A. Buchanan, D. Markiewicz, T. K. Cox, A. Chakravarti, M. Buchwald, and L. -C. Tsui, "Identification of the cystic fibrosis gene: genetic analysis," *Science*, vol 245, pp 1073–1080, 1989; J. R. Riordan, J. M. Rommens, B. -S. Kerem, N. Alon, R. Rozmahel, Z. Grzelczak, J. Zielenski, S. Lok, N. Plavsic, J. -L. Chou, M. L. Drumm, M. C. Iannuzzi, F. S. Collins, and L. -C. Tsui, "Identification of the cystic fibrosis gene: cloning and characterization of complementary DNA," *Science*, vol. 245, pp. 1066–1073, 1989), incorporated by reference.

SUMMARY OF THE INVENTION

The present invention pertains to a method for genotyping. The method comprises the steps of obtaining nucleic acid material from a genome. Then there is the step of amplifying a location of the material. Next there is the step of assaying the amplified material based on size and concentration. Then there is the step of converting the assayed amplified material into a first set of electrical signals corresponding to size and concentration of the amplified material at the location. Then there is the step of operating on the first set of electrical signals produced from the amplified material with a second set of electrical signals corresponding to a response pattern of the location to produce a third set of clean electrical signals corresponding to the size and multiplicities of the unamplified material on the genome at the location.

The present invention also pertains to a system for genotyping. The system comprises means or a mechanism for obtaining nucleic acid material from a genome. The system also comprises means or a mechanism for amplifying a location of the material. The amplified means or mechanism is in communication with the nucleic acid material. Additionally, the system comprises means or a mechanism for assaying the amplified material based on the size and concentration. The assaying means or mechanism is in communication with the amplifying means or mechanism. The system moreover comprises means or a mechanism for converting the assayed amplified material into a first set of electrical signals corresponding to size and concentration of the amplified material at the location. The converting means or mechanism is in communication with the assaying means. The system for genotyping comprises means or a mechanism for operating on the first set of electrical signals produced from the amplified material with a second set of electrical signals corresponding to a response pattern of the location to produce a third set of clean electrical signals corresponding to the size and multiplicities of the unamplified material on the genome at the location. The operating means or mechanism is in communication with the sets of electrical signals. The present invention also pertains to a method of analyzing genetic material of an organism. The present invention additionally pertains to a method for producing a gene.

BRIEF DESCRIPTION OF THE DRAWINGS

In the accompanying drawings, the preferred embodiment of the invention and preferred methods of practicing the invention are illustrated in which:

FIG. 1B is a flow chart of a method for genotyping polymorphic genetic loci.

FIG. 3A shows computed base size vs. peak area for representative individuals and loci from the image analysis. The DNA concentrations shown were detected and quantitated at every DNA length (rows) for each genotyped individual (columns). The peak area values were computed by the system from the raw data files corresponding to FIG. 2, are in arbitrary units, and have been rounded to the nearest integer. Zero values denote minimal signal. The numbers illustrate the three classes of CA-repeat genotype data: hemizygote/homozygote alleles, distinct heterozygote alleles, or superimposed heterozygote alleles.

FIG. 6 is a flow chart of a system for diagnosing genetic disease.

DESCRIPTION OF THE PREFERRED EMBODIMENT

Figure 1A:
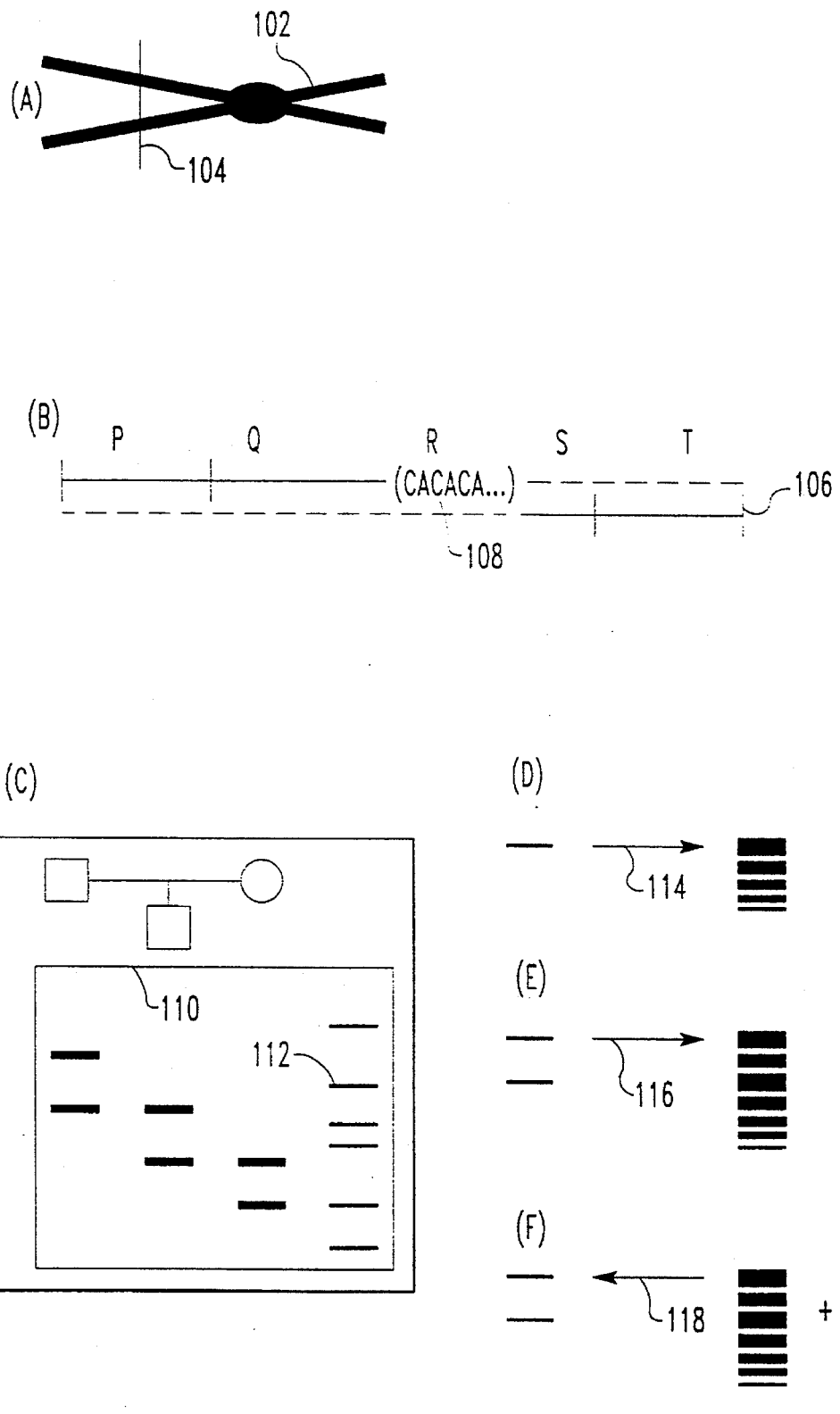
FIG. 1A is a schematic of a problem addressed by this invention. Shown is (a) a paired autosomal chromosome and a marker location, (b) a CA-repeat genetic marker location, (c) a sizing assay done by gel electrophoresis, (d) the PCR corruption response pattern of one allele, (e) the superimposed corrupted pattern of two alleles, and (f) the recovery of the allele sizes by combining the two allele corrupted pattern with the one allele response pattern.

A genome is any portion of the inherited nucleic acid material, or its derivatives, of one or more individuals of any species. In particular, it is used as a sample for characterization or assay.

A nucleic acid material from a genome is a sampling of nucleic acids derived from individuals having some portion of that genome. This represents the unknown material that is to be genotyped.

A location on a genome is a physical region that does not exceed 10 megabases that is defined by a set of nucleic acid sequences that characterize the amplification of that region. In the preferred embodiment, a location is more specifically a polymorphic polynucleotide repeat locus that is defined by its pair of PCR primers.

A set of electrical signals entails electromagnetic energies, including electricity and light, that serves as a physical mechanism for containing and transferring information, preferably in a computing device.

The first set of electrical signals corresponds to a series of nucleic acid size and concentration features that assay the amplification products of a location on a genome. For instance, these signals can include artifacts such as PCR stutter or background noise.

The second set of electrical signals corresponds to a series of nucleic acid size and concentration features that characterize the response pattern of a single sequence of a location when distorted by an amplification procedure. These features may vary as a function of the size of the sequence at the location, and there is at least one (though not more than fifty) response pattern associated with the location. For instance, these response patterns can include a PCR stutter artifact of a location on a genome, or background noise.

The third set of clean electrical signals corresponds to the size and multiplicities of the genome material at a location on a genome. More specifically, the clean electrical signals corresponds to the different alleles present at a location on a genome, and their relative numbers. For instance, these clean signals may have the artifacts (such as PCR stutter or background noise) removed.

A stutter-based multiplexed genotyping is a mechanism for assaying one or more amplified locations of nucleic acid material from a genome. More specifically, the ranges of allele sizes corresponding to each location need not be disjoint. For instance, this enables multiple location assays to be done simultaneously (a) within the same size window, or (b) without regard to any size window.

A convolution is a first set of signals formed by superimposing a second set of signals in proportions determined by a third set of signals. A convolution is not necessarily linear shift-invariant, that is, the signals in the second set need not be identical.

A deconvolution is a determination of a third set of signals by means of numerical operations on a first set of signals and a second set of signals, wherein the first set of signals is described by a convolution of the second set of signals with the third set of signals. A deconvolution is not necessarily linear shift-invariant, that is, the signals in the second set need not be identical.

(1) A method and system for genotyping polymorphic genetic loci.

Referring to FIG. 1B, a method is described for genotyping that is comprised of the steps:

(1) obtaining nucleic acid material from a genome;

(2) amplifying a location of the material;

(3) assaying the amplified material based on size and concentration;

(4) converting the assayed amplified material into a first set of electrical signals corresponding to size and concentration of the amplified material at the location;

(5 or 5', 6) operating on the first set of electrical signals produced from the amplified material with a second set of electrical signals corresponding to a response pattern of the location to produce a third set of clean electrical signals corresponding to the size and multiplicities of the material at the location.

Referring to FIG. 1B, step 1 is for obtaining nucleic acid material from a genome.

The process begins by extracting DNA from blood or tissue. There are numerous standard methods to isolate DNA including whole blood, isolated lymphocytes, tissue, and tissue culture (Ausubel, F. M., Brent, R., Kingston, R. E., Moore, D. D., Seidman, J. G., Smith, J. A., and Struhl, K., ed. 1993. *Current Protocols in Molecular Biology.* New York, N.Y.: John Wiley and Sons; Sambrook, J., Fritsch, E.

F., and Maniatis, T. 1989. *Molecular Cloning, second edition.* Plainview, N.Y.: Cold Spring Harbor Press; Nordvag 1992. Direct PCR of Washed Blood Cells. *BioTechniques,* 12(4): 490–492), incorporated by reference. In the preferred embodiment, DNA is extracted from anticoagulated human blood removed by standard venipuncture and collected in tubes containing either EDTA or sodium citrate. The red cells are lysed by a gentle detergent and the leukocyte nuclei are pelleted and washed with the lysis buffer. The nuclei are then resuspended in a standard phosphate buffered saline (pH=7.5) and then lysed in a solution of sodium dodecyl sulfate, EDTA and tris buffer pH 8.0 in the presence of proteinase K 100 ug/m l. The proteinase K digestion is performed for 2 hours to overnight at 50° C. The solution is then extracted with an equal volume of buffered phenol-chloroform. The upper phase is reextracted with chloroform and the DNA is precipitated by the addition of NaAcetate pH 6.5 to a final concentration of 0.3M and one volume of isopropanol. The precipitated DNA is spun in a desktop centrifuge at approximately 15,000 g, washed with 70% ethanol, partially dried and resuspended in TE (10 mM Tris pH 7.5, 1 mM EDTA) buffer. There are numerous other methods for isolating eukaryotic DNA, including methods that do not require organic solvents, and purification by adsorption to column matrices. None of these methods are novel, and the only requirement is that the DNA be of sufficient purity to serve as templates in PCR reactions and in sufficient quantity.

Referring to FIG. 1B, step 2 is for amplifying a location of the material.

The genomic DNA is then amplified at one or more locations on a genome, in the preferred embodiment, via a PCR reaction. Size standards are used to calibrate the quantitative analysis. The methods for this PCR amplification given here are standard, and can be readily applied to every microsatellite or polynucleotide repeat marker that corresponds to a (relatively unique) location on a genome.

Polymorphic genetic markers are locations on a genome that are selected for examining a genome region of interest. The genetic markers to be used for each polynucleotide repeat are obtained as PCR primer sequences pairs and PCR reaction conditions from available databases (Genbank, GDB, EMBL; Hilliard, Davison, Doolittle, and Roderick, Jackson laboratory mouse genome database, Bar Harbor, Me.; SSLP genetic map of the mouse, Map Pairs, Research Genetics, Huntsville, Ala.), incorporated by reference. Alternatively, some or all of these microsatellite locations can also be constructed using existing techniques (Sambrook, J., Fritsch, E. F., and Maniatis, T. 1989. *Molecular Cloning, second edition.* Plainview, N.Y.: Cold Spring Harbor Press; N. J. Dracopoli, J. L. Haines, B. R. Korf, C. C. Morton, C. E. Seidman, J. G. Seidman, D. T. Moir, and D. Smith, ed., *Current Protocols in Human Genetics.* New York: John Wiley and Sons, 1994), incorporated by reference.

The oligonucleotide primers for each polynucleotide repeat genetic marker are synthesized (Haralambidis, J., Duncan, L., Angus, K., and Tregear, G. W. 1990. The synthesis of polyamideoligonucleotide conjugate molecules. *Nucleic Acids Research,* 18(3): 493–9. Nelson, P. S., Kent, M., and Muthini, S. 1992. Oligonucleotide labeling methods. 3. Direct labeling of oligonucleotides employing a novel, non-nucleosidic, 2-aminobutyl-1,3-propanediol backbone. *Nucleic Acids Research,* 20(23): 6253–9. Roget, A., Bazin, H., and Teoule, R. 1989. Synthesis and use of labelled nucleoside phosphoramidite building blocks bearing a reporter group: biotinyl, dinitrophenyl, pyrenyl and dansyl. *Nucleic Acids Research,* 17(19): 7643–51. Schubert, F., Cech, D., Reinhardt, R., and Wiesner, P. 1992. Fluorescent labelling of sequencing primers for automated oligonucleotide synthesis. *Dna Sequence,* 2(5): 273–9. Theisen, P., McCollum, C., and Andrus, A. 1992. Fluorescent dye phosphoramidite labelling of oligonucleotides. *Nucleic Acids Symposium Series,* 1992(27): 99–100.), incorporated by reference. These primers may be derivatized with a fluorescent detection molecule or a ligand for immunochemical detection such as digoxigenin. Alternatively, these oligonucleotides and their derivatives can be ordered from a commercial vendor (Research Genetics, Huntsville, Ala.).

In the preferred embodiment, the genomic DNA is mixed with the other components of the PCR reaction at 4° C. These other components include, but are not limited to, the standard PCR buffer (containing Tris pH 8.0, 50 mM KCl, 2.5 mM magnesium chloride, albumin), triphosphate deoxynucleotides (dTTP, dCTP, dATP, dGTP), the thermostable polymerase (e.g., Taq polymerase). The total amount of this mixture is determined by the final volume of each PCR reaction (say, 10 ul) and the number of reactions.

The PCR reactions are performed on all of the reactions by heating and cooling to specific locus-dependent temperatures that are given by the known PCR conditions. The entire cycle of annealing, extension, and denaturation is repeated multiple times (ranging from 20–40 cycles depending on the efficiencies of the reactions and sensitivity of the detection system) (Innis, M. A., Gelfand, D. H., Sninsky, J. J., and White, T. J. 1990. *PCR Protocols: A Guide to Methods and Applications.* San Diego, Calif.: Academic Press.), incorporated by reference. In the preferred embodiment, for STR CA-repeat loci, the thermocycling protocol on the Perkin-Elmer PCR System 9600 machine is:

a) Heat to 94° C. for 3' b) Repeat 30x:
   94° C. for ½' (denature)
   53° C. for ½' (anneal)
   65° C. for 4' (extend)

c) 65° C. for 7' (extend)

d) 4° C. soak ad librum

The PCR cycles are completed, with each reaction tube containing the amplified DNA from a specific location of the genome. Each mixture includes the DNA that was synthesized from the two alleles of the diploid genome (a single allele from haploid chromosomes as is the case with the sex chromosomes in males or in instances of cells in which a portion of the chromosome has been lost such as occurs in tumors, or no alleles when both are lost). If desired, the free deoxynucleotides and primers may be separated from the PCR products by filtration using commercially available filters (Amicon, "Purification of PCR Products in Microcon Microconcentrators," Amicon Beverly Mass., Protocol Publication 305; A. M. Krowczynska and M. B. Henderson, "Efficient Purification of PCR Products Using Ultrafiltration," *BioTechniques,* vol. 13, no. 2, pp. 286–289, 1992), incorporated by reference.

In the preferred embodiment, these PCR reactions generate quantifiable signals, and are done either separately or in multiplexed fashion. In one multiplexed embodiment for DMD diagnosis, four CA-repeat markers [3'-CA (C. Oudet, R. Heilig, and J. Mandel, "An informative polymorphism detectable by polymerase chain reaction at the 3' end of the dystrophin gene," *Hum Genet,* vol. 84, pp. 283–285, 1990), 5'DYSII (C. Feener, F. Boyce, and L. Kunkel, "Rapid detection of CA polymorphisms in cloned DNA: application to the 5' region of the dystrophin gene," *Am J Hum Genet,* vol. 48, pp. 621–627, 1991), and STRs 45 and 49 (P.

Clemens, R. Fenwick, J. Chamberlain, R. Gibbs, M. de Andrade, R. Chakraborty, and C. Caskey, "Linkage analysis for Duchenne and Becker muscular dystrophies using dinucleotide repeat polymorphisms," *Am J Hum Genet*, vol 49, pp 951–960, 1991), incorporated by reference, distributed throughout the 2.5 Mb dystrophin gene are used. The forward primer of each pair of PCR amplimers is covalently linked to fluorescein, and all four loci are amplified in a single 25 cycle multiplex PCR reaction (L. S. Schwartz, J. Tarleton, B. Popovich, W. K. Seltzer, and E. P. Hoffman, "Fluorescent Multiplex Linkage Analysis and Carrier Detection for Duchenne/Becker Muscular Dystrophy," *Am. J. Hum. Genet.*, vol. 51, pp. 721–729, 1992), incorporated by reference. The mixed fluorescent primers can be stored for over three years with no loss of label intensity, obviating the need for relabelling prior to each experiment. Two fluorescent molecular weight standards (dystrophin gene exons 50 (271 bp) and 52 (113 bp) (A. Beggs and L. Kunkel, "A polymorphic CACA repeat in the 3' untranslated region of dystrophin," *Nucleic Acids Res*, vol 18, pp. 1931, 1990; L. S. Schwartz, J. Tarleton, B. Popovich, W. K. Seltzer, and E. P. Hoffman, "Fluorescent Multiplex Linkage Analysis and Carrier Detection for Duchenne/Becker Muscular Dystrophy," *Am. J. Hum. Genet.*, vol. 51, pp. 721–729, 1992), incorporated by reference, are added to samples prior to electrophoresis. These four markers cover the full spectrum of CA-repeat sizes, signals, stutter patterns, and polymorphisms, which demonstrates that the data generation and analysis methods described in this patent applications are applicable to the entire class of di- and polynucleotide repeat markers.

Referring to FIG. 1B, step 3 is for assaying the amplified material based on size and concentration.

In the preferred embodiment, size separation of the labeled PCR products is done by gel electrophoresis on polyacrylamide gels (Ausubel, F. M., Brent, R., Kingston, R. E., Moore, D. D., Seidman, J. G., Smith, J. A., and Struhl, K., ed. 1993. *Current Protocols in Molecular Biology*. New York, N.Y.: John Wiley and Sons; N. J. Dracopoli, J. L. Haines, B. R. Korf, C. C. Morton, C. E. Seidman, J. G. Seidman, D. T. Moir, and D. Smith, ed., *Current Protocols in Human Genetics*. New York: John Wiley and Sons, 1994; Sambrook, J., Fritsch, E. F., and Maniatis, T. 1989. *Molecular Cloning, second edition*. Plainview, N.Y.: Cold Spring Harbor Press), incorporated by reference. The gel image is then put into machine readable digital format. This is done by electronic scanning of a gel image (e.g., autoradiograph) using a conventional gray scale or color scanner, by phosphor imaging, or by direct electronic acquisition using an automated DNA sequencer (e.g., fluorescence-based) for sizing DNA products.

This sizing assay acquires signals that enable the eventual quantitation of the nucleic acid sizes and concentrations present in the amplified material. This is done by obtaining features (related to size and concentration) of the differentially sized nucleic acid products in the amplified material that can be converted into electrical signals. This acquisition may be accomplished by generating images that can be scanned into electronic pixels, by applying a photomultiplier tube to fluorescently labeled amplified material thereby generating electrical signals, by measuring labeled amplified material in electrophoretic gels, including ultrathin capillary arrays (R. A. Mathies and X. C. Huang, *Nature*, vol. 359, pp. 167, 1992), incorporated by reference, and ultrathin slabs (A. J. Kostichka, *Bio/Technology*, vol. 10, pp. 78, 1992), incorporated by reference, by mass spectrometry (K. J. Wu, A. Stedding, and C. H. Becker, *Rapid Commun. Mass Spectrom.*, vol. 7, pp. 142, 1993), incorporated by reference, by multiplexed hybridization entailing processing a mixture of genotyping templates followed by sequential hybridization to reveal the invidual allele patterns on a membrane (G. M. Church and S. Kieffer-Higgins, "Multiplex DNA sequencing," *Science*, vol. 20, pp. 185, 1988; J. L. Cherry, H. Young, L. J. DiSera, F. M. Ferguson, A. W. Kimball, D. M. Dunn, R. F. Gesteland, and R. B. Weiss, "Enzyme-Linked Fluorescent Detection for Automated Multiplex DNA Sequencing," *Genomics*, vol. 20, pp 68–74, 1994), incorporated by reference, by performing differential hybridization of nucleic acid probes with the amplified material, other automation mechanisms (J. S. Ziegle and et.al., "Application of automated DNA sizing technology for genotyping microsatellite loci," *Genomics*, vol. 14, pp 1026–1031, 1992), incorporated by reference, or by any other physical means of detecting relative concentrations of nucleic acid species. The acquisition of the sizing assay data may be effected in real-time, or be postponed to allow increased accumulation of nucleic acid signals.

A preferred embodiment using an automated DNA sequencer is given for the specific case of DMD diagnosis; this procedure can be used for any STR PCR product. The PCR products of each of the four DMD CA-repeat loci may lie their own individual lane, or be multiplexed into multiple (e.g., four) minimally overlapping size windows of a single lane. In the latter case, the alleles for all four loci and the molecular weight markers can be read out as a size-multiplexed signal in one lane of a DNA sequencer. The DuPont Genesis DNA sequencer can generate fluorescent intensity data for 10–12 lanes, with one lane assigned to each individual. In an alternative embodiment, the multiple lanes of the Applied Biosystems sequencer (ABI 373A, with optional Genotyper software), incorporated by reference, the Pharmacia sequencer, the Millipore sequencer, or any comparable system for direct electronic acquisition of electrophoretic gel images is used.

Figure 2:
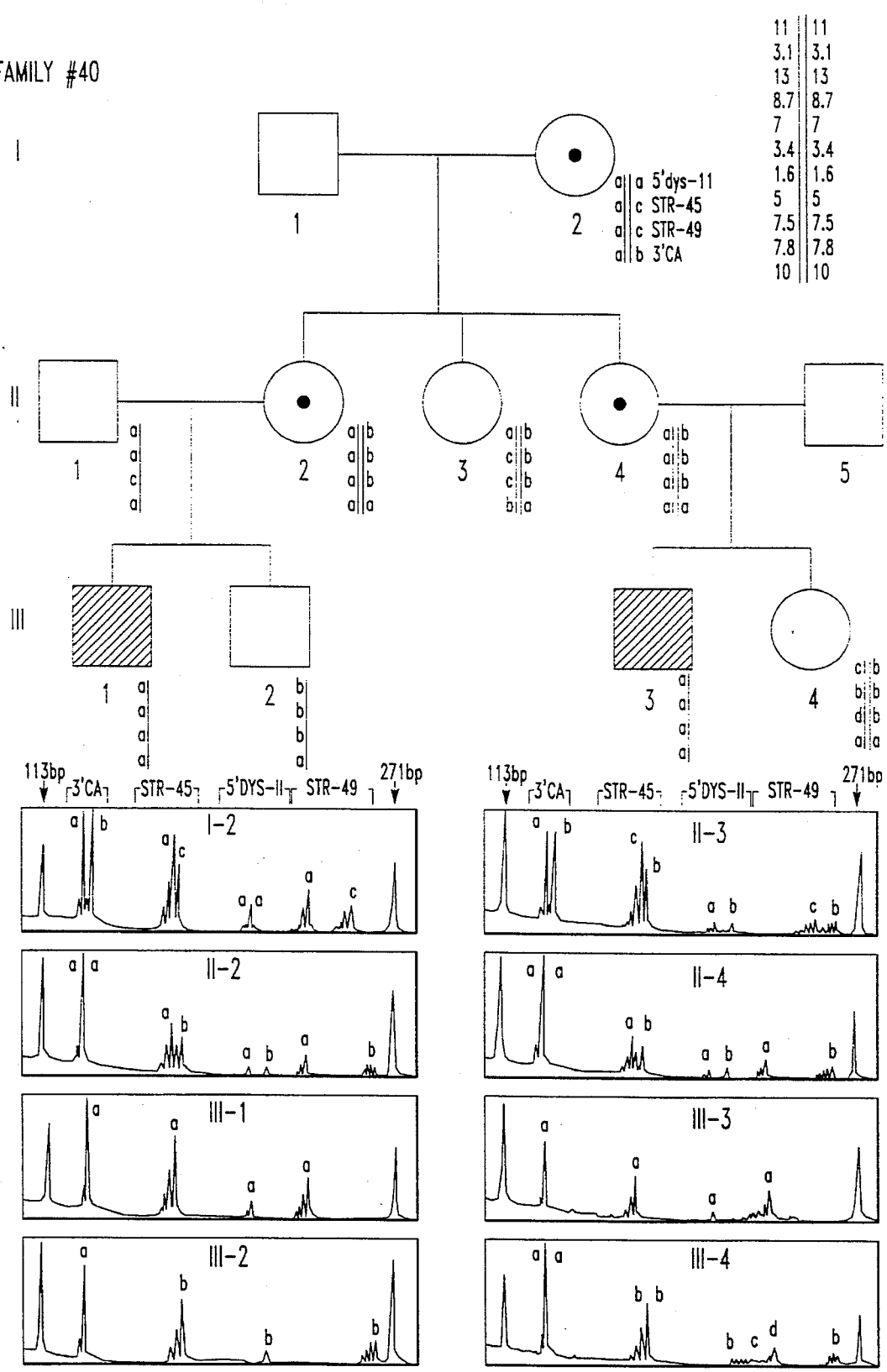
FIG. 2 is a PMT voltage versus time data used for input into automated genotyping. Shown is a Becker muscular dystrophy family (family #40), with representative lane data from the automated sequencer shown below. Multiplex fluorescent CA repeat analysis was done as previously described (Schwartz et al. 1992). The time windows corresponding to each of four dinucleotide repeat loci are shown above the data traces. The four dystrophin gene CA repeat loci show the full range of different patterns observed with most CA-repeats: 3'CA shows very clean, distinct alleles but is not very informative, whereas STR-49 and STR-45 show complex patterns of 6–7 peaks for each allele. Reprinted from Schwartz et al. (1992).

With the DuPont system, at least ten family members can be haplotyped for the dystrophin gene with a single sequencer run. Each lane's signal intensity is observed as photomultiplier tube (PMT) voltage units (12 bit resolution), and is sampled by the sequencer every 3 seconds, providing roughly 20 data points per base of DNA. Gels are run for a total of 4 hours, generating approximately 5,000 data points per lane (individual). Machine readable data files from the sequencer runs, recorded as a linear fluorescence signal (PMT voltage) trace for each lane (individual), are automatically generated by the Genesis 2000 software. The traces for the running example analysis of Family #40 are shown in FIG. 2. These time vs. voltage files are entered into the system, as described below.

Referring to FIG. 1B, step 4 is for converting the assayed amplified material into a first set of electrical signals corresponding to size and concentration of the amplified material at the location.

The signals obtained in step 3 from the differentially sized amplified nucleic acid material of a location on a genome are converted in step 4 into a first set of electrical signals corresponding to size and concentration features of the amplified material. The conversion is effected using a computer device with memory via a program in memory that examines the values of the assay signals residing in memory locations. These values are assessed for features corresponding to the detection of a discrete size region of amplified nucleic acid material, such as a peak or band in the differential sizing assay. The relative concentration of nucleic acid material is then quantitated in such regions. These size/ concentration features are then stored as a first set of electrical signals in the computer's memory, for use in step 5.

Figure 3B:
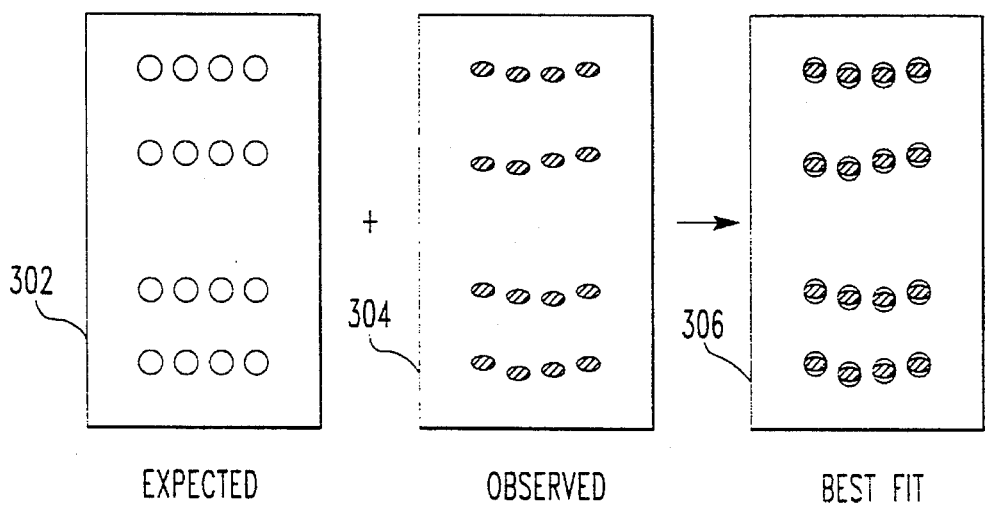
FIG. 3B shows the determination of allele sin and concentrations by applying a grid of expected locations to the data image using relaxation methods and local quantitation. This is done for finding molecular weight markers.

In a preferred embodiment, each individual's preprocessed DuPont data file contains a time vs. intensity trace of the single or multiplexed PCR sequencer run generated from the corresponding gel lane. For quantitative processing, these data are converted to DNA size vs. DNA concentration units. The system first searches predetermined time regions to find the molecular weight markers (dystrophin gene exons 50 [271 bp] and 52 [113 bp]). A linear interpolation is then performed to construct a time vs. size mapping grid. Each predefined CA-repeat locus is then processed independently within its predefined size window. Every peak within the CA-repeat marker region is identified, and is assigned a time and an area. The apex of a peak is defined as the point of change between a monotonically increasing series and a monotonically decreasing series, left to right. The monotonicity predicate holds when the difference between an average of right values and an average of left values exceeds a predetermined threshold. Using the linear time-to-size interpolation from the grid, the time of each peak apex's occurrence is converted to a DNA size estimate. The areas are computed as the full-width at half-max peak from the intensity data, and are considered to be proportional to the approximate DNA concentration for any specific locus. FIG. 3A shows partial DNA size/intensity results from the machine vision analysis of example Family #40.

In an alternative embodiment, the two dimensional image data (rather than the one dimensional preprocessed lane data) is analyzed to produce size vs. intensity information. First, the image locations of the molecular weight (MW) markers are found in every lane in which they were placed. This is done by searching for peaks of the proper shapes in the expected image locations (H. A. Drury, K. W. Clark, R. E. Hermes, J. M. Feser, L. J. Thomas Jr., and H. Donis-Keller, "A Graphical User Interface for Quantitative Imaging and Analysis of Electrophoretic Gels and Autoradiograms," *BioTechniques,* vol. 12, no. 6, pp. 892–901, 1992), incorporated by reference. By comparing the observed MW marker peak locations to their expected peak locations, a linear interpolation is established that maps each two dimensional image location to a unique lane and DNA size. Second, the data peaks of the stuttered genetic marker alleles are found on the image. For each peak, its lane and DNA size is determined by linear interpolation, and the observed intensity is summed over the peak region; the lane, DNA size, and signal intensity are then recorded. With superimposed signals (e.g., using multiple fluorescent probes) in each lane, the image plane is noted as well. To adjust background levels, standard machine vision techniques such as iterative thresholding are used (J. R. Parker, *Practical Computer Vision Using C.* New York: John Wiley and Sons, 1994), incorporated by reference.

For quantitative sizing, predetermined MW markers are used as size reference standards. In the preferred embodiment, these are placed every 1–50 base pairs in a predetermined region of the gel lane (10 bp ladder, BioVentures, Murphysburgh, Tenn.). These markers may be superimposed on the same lane as the genetic marker data (e.g., when using multicolor fluorescent labels), or be run in an adjacent lane (e.g., when using radioactive labels). For additional accuracy in quantitative sizing, the electrophoretic migration of each polynucleotide-repeat genetic marker can be calibrated to the migration of the MW sizing markers. In an alternative embodiment for size calibration, polynucleotide markers from individuals having a predetermined genotype (e.g., from CEPH, France) are used; the stutter bands, as well as the allelic bands, are useful here in establishing the DNA sizes. In another alternative embodiment, a reproducible DNA sequencing ladder subset (e.g., the A's or T's of an M13 ladder) is used.

In an alternative embodiment, a general expectation-based architecture is used. The expected locations of MW and genetic markers are made representationally explicit, and relaxation methods are then employed. First, referring to FIG. 3B, the known expected locations 302 of the MW markers are arranged into a data structure, which makes explicit the local horizontal and vertical pairwise distance relationships between neighboring markers. The image locations 304 of the MW markers are then found in every lane with MW markers, by searching for peaks of the proper shapes in the expected locations. The observed MW marker peak locations are then compared with their expected peak locations. A relaxation process is then performed which heuristically minimizes the local horizontal and vertical pairwise distances, adapting the expected grid to the observed data, and produces a "best fit" 306 of the observed locations to the expected locations. This produces a local linear interpolation mapping in each region of the grid, that maps each two dimensional image location to a unique lane and DNA size.

Figure 3C:
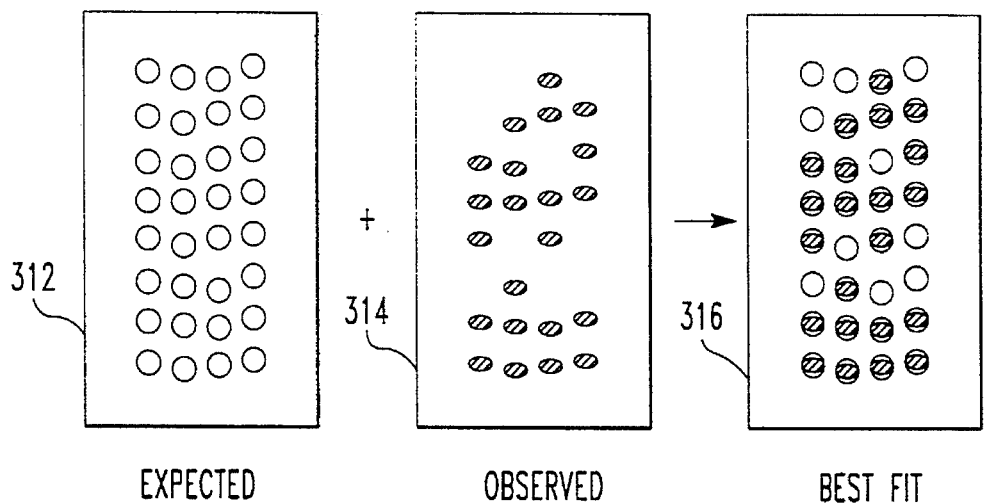
FIG. 3C shows the determination of allele sizes and concentrations by applying a grid of expected locations to the data image using relaxation methods and local quantitation. This is done for finding genetic marker dam locations.

Second, referring to FIG. 3C the data peaks of the stuttered genetic marker alleles are found on the image. The possible expected locations 312 of genetic marker peaks are arranged into a data structure, which makes explicit the local horizontal and vertical pairwise distance relationships between markers as interpolated from the MW marker analysis. The image locations 314 of the genetic markers are then found by searching for peaks of the proper shapes in the image locations predicted by the expectation grid. A relaxation process is then performed which heuristically minimizes the local horizontal and vertical pairwise distances between observed data peaks, adapting the expected data position grid to the observed data positions, thereby producing a "best fit" 316 of the observed locations to the expected locations. This determines, for each observed data peak, the lane/plane position and the DNA size; the observed intensity at that point is then summed over the peak region, and the lane/plane, DNA size, and signal intensity are recorded. When inheritance information between related individuals is available, the consistency between the predicted inheritance of alleles and observed allele peak patterns can be used to further align the predicted and observed data peak grids.

Referring to FIG. 1B, step 5 is for operating on the first set of electrical signals produced from the amplified material with a second set of electrical signals (described in step 6) corresponding to a response pattern of the location to produce a third set of clean electrical signals corresponding to the size and multiplicities of the unamplified material on the genome at the location.

The measured first set of electrical signals produced from the amplified material is corrupted by the response pattern of the location on the genome. The objective is to produce a third set of clean electrical signals corresponding to the size and multiplicities of the unamplified material on the genome at the location. This is done by operating on the first set of electrical signals, together with the second set of electrical signals detailed in step 6, using a program residing in the memory of the computer. In the preferred embodiment, this operation is a deconvolution procedure.

For a genome of one individual, the pattern of measured peaks (DNA sizes vs. DNA concentrations) is classified into one of three classes: hemizygote/homozygote alleles, distinct heterozygote alleles, or superimposed heterozygote alleles. These three classes of peak patterns are defined as follows. A hemizygote/homozygote allele comprises a single decay pattern of decreasing peak amplitudes, with DNA size decreasing from right to left (FIG. 2); the rightmost and largest peak is considered to be the primary peak. For example, individual A of family #40 is a male X-linked hemizygote. At locus STR-45, using the values shown in FIG. 3A, the peak occurs at length 171 nucleotides, with a concentration of 101,299. Thus, the genotype of individual A at locus STR-45 is assigned the value 171. The peak pattern is classified as distinct heterozyogote when two such decay patterns are found within the marker window, and the two primary peaks are of similar amplitude. For example, individual D of family #40 is heterozygotic at locus STR-49. As seen in FIG. 3A, there is one peak at length 233, and a second peak at length 264. The stutter peaks are widely separated, so there was no overlap in their stutter patterns, and the genotype was readily determined from the two distinct simple signals to be (233, 264). The third class, superimposed heterozygote alleles, is invoked when no simple pattern of alleles satisfying the hemizygotic/homozygotic or distinct heterozygotic criteria is detected. In this class, present in heterozygote loci, the alleles are closely spaced, and produce a complex pattern of overlapping peaks. Deconvolution of the peak pattern is then invoked to identify the two alleles. Since the peak decay patterns are similar for any given locus, the deconvolution of a complex heterozygous pattern at a locus can be done with respect to the hemizygous decay pattern (of a different individual) at the same locus.

With superimposed heterozygote alleles, the overlapping stutter peaks of proximate alleles at a locus are deconvolved, thereby computing a single peak per allele. For any given STR marker locus, the allele stutter pattern is relatively fixed. The relative DNA concentrations for one allele at a preset (discrete) DNA allele size can be written as the pattern vector $$\langle p_n, \ldots, p_2, p_1, p_0 \rangle,$$

or, equivalently, as the polynomial $p(x)$, $$p(x) = p_n * x^n + \ldots + p_2 * x^2 + p_1 * x + p_0.$$

Each coefficient $p_k$ is the observed peak area in the allele's pattern for the $k^{th}$ stutter peak.

The superimposed stutter patterns observed in the sequencer data of heterozygotic markers can be similarly described by a polynomial $q(x)$. The coefficients of $q(x)$ are the superimposed peak areas produced by PCR stuttering of the two alleles. The PCR stutter of each allele has a fixed pattern described by the polynomial $p(x)$. When the allele contains precisely r repeated dinucleotides, the pattern is shifted 2r bases on the sequencer gel lane. (With repeated trinucleotides, tetranucleotides, and other non-dinucleotide STRs, this factor may be different from "2", but the method still obtains.) A shift in the stutter pattern by 2r bases mathematically corresponds to multiplication of the polynomial $p(x)$ by $x^{2r}$. Therefore, if the two allele sizes are s and t, then the two stuttered alleles produce the shifted polynomials $$x^s * p(x), \text{ and } x^t * p(x),$$

respectively. Superimposing these two allele stutter patterns produces the observed sum $$\begin{aligned} q(x) &= x^s * p(x) + x^t * p(x), \text{ or} \\ &= (x^s + x^t) * p(x). \end{aligned}$$

Direct deconvolution to obtain the allele sizes s and t (hence, the genotype) by polynomial division via $$q(x)/p(x) = x^s + x^t$$

is one embodiment of the deconvolution process. However, when this approach is not sufficiently robust with actual data containing noise, a preferred embodiment employing statistical moment computations is used. This embodiment is more robust in the presence of noise, and requires only linear time computation. Moment computations were also used in (A. Papoulis, "Approximations of Point Spreads for Deconvolution," *J. Opt Soc. Am.*, vol 62, no. 1, pp. 77–80, 1972), incorporated by reference.

The $k^{th}$ moment of a polynomial $u(x)$ is $$u_k = u^{(k)}(1),$$

where $u^{(k)}$ is the $k^{th}$ algebraic derivative of $u(x)$. $u_k$ can be rapidly computed by weighted summation of the coefficients of $u(x)$'s $k^{th}$ derivative. As derived below, $$s + t = (q_1 - 2p_1)/p_0,$$

$$s^2 + t^2 = \{[q_2 - 2p_2] + (s+t)[p_0 - 2p_1]\}/p_0, \text{ and}$$

$$(s-t)^2 = 2(s^2 + t^2) - (s+t)^2.$$

Therefore, one can directly calculate the allele sizes as $$s = [(s+t) + (s-t)]/2, \text{ and}$$

$$t = [(s+t) - (s-t)]/2.$$

This computation has the effect of deconvolving the superimposed PCR stutter patterns of the heterozygotic alleles into the two discrete peaks, having size s and t, needed for straightforward genotyping. The real numbers s and t are rounded (up or down) to the nearest integer occurring in the observed peak data.

Consider, for example, the STR-45 locus of individual E of Family #40. The DNA concentrations at the PCR product sizes 161 through 173 are given in FIG. 3A. The sizes and concentrations can be represented by the polynomial $$q(x) = 61326x^{173} + 94852x^{171} + 47391x^{169} + 18115x^{167} + 5896x^{165} + 1928x^{163} + 930x^{161}.$$

This pattern does not conform to a simple uniform decay. In Family #40, individual A's hemizygotic locus STR-45, does (as expected) have a simple decay pattern from the peak at size 171 down through size 161, as seen in FIG. 3A. This data can similarly be represented by the polynomial $$p(x) = 101299x^{171} + 55373x^{169} + 20799x^{167} + 7242x^{165} + 2171x^{163} + 821x^{161},$$

and can be used to help recover the two alleles at individual E's STR-45 locus.

As just described, individual E's peak pattern at locus STR-45 can be viewed as the superposition of two shifted copies of A's peak pattern at STR-45. Conceptually, the observed $q(x)$ pattern is the sum of two shifted copies of $p(x)$:

$$q(x) = x^s * p(x) + x^t * p(x), \text{ or}$$
$$= (x^s + x^t) * p(x).$$

Deconvolution of $q(x)$ with respect to $p(x)$ determines $(x^s+x^t)$, where s and t are the peaks of the shifted patterns. That is, s and t provide the genotype. The polynomial coefficients are first renormalized to account for the expectation that $p(x)$ measures a single chromosome dosage, whereas $q(x)$ measures two doses. Then, using the polynomial moment technique detailed above, and shifting the sizes to their correct origin, compute s=173.061, and t=170.832.

Figure 4:
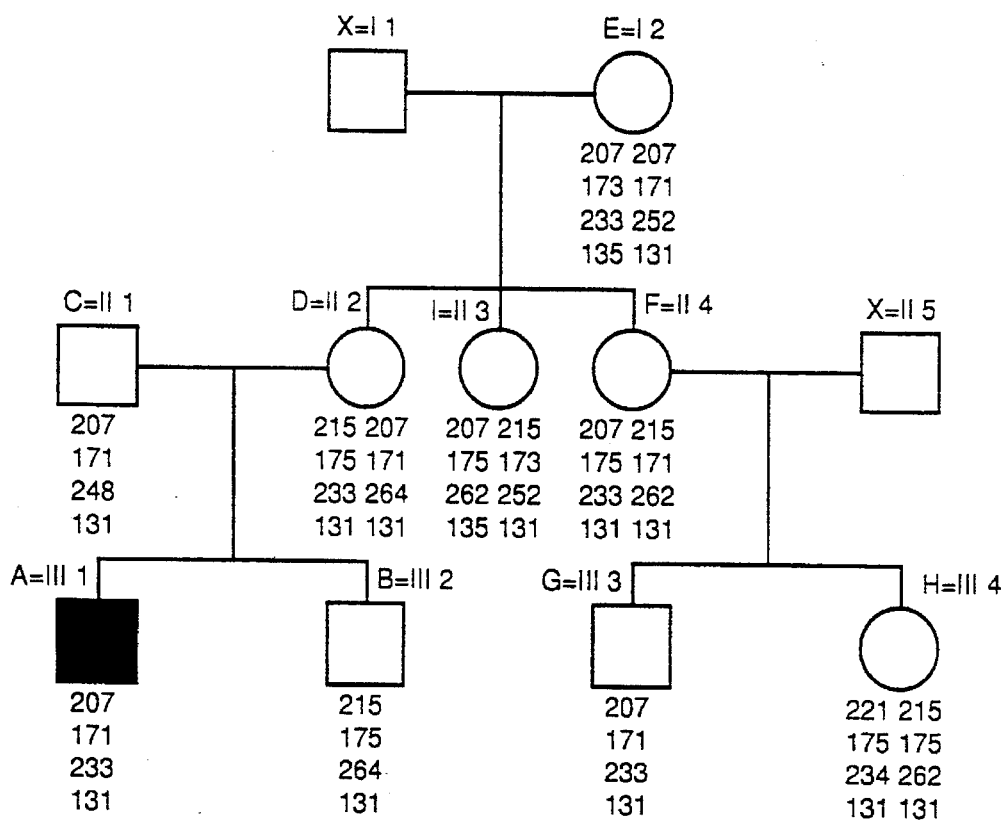
FIG. 4 is the output from the pedigree construction and genotyping modules. Shown are the genotypes that the software automatically computed for each tested member of Family #40 (FIG. 2). The software automatically applied one of three methods (maximum of single peak, maxima of double peaks, or allele deconvolution) most appropriate to the locus data. This diagram was drawn by the graphical display component of the system.

Rounding these numbers to the closest integers in the peak pattern, yields the genotype (173, 171). This example result illustrates how PCR stutter peaks can be effectively exploited using the described deconvolution approach to automatically resolve CA-repeats of close sizes. FIG. 4 shows the genotyping results using these methods for every member of example Family #40.

The following is a detailed derivation of this deconvolution procedure for recovering the alleles s and t in the presence of PCR stutter peaks from the data $q(x)$, using $p(x)$. $p(x)$ is immediately known in X chromosome family data from (haploid) male individuals, and can be derived via similar deconvolution procedures for autosomal loci. One proceeds in four steps.

Step 5a. Computing an expression for the allele sum s+t. Taking the derivatives of both sides of $$q(x)=p(x) * (x^s+x^t),$$

yields $$d/dx \, [q(x)] = d/dx \, [p(x) * (x^s + x^t)]$$
$$= d/dx \, [p(x)] * (x^s + x^t) + p(x) * d/dx \, [x^s + x^t],$$
$$= p^{(1)}(x) * (x^s + x^t) + p(x) * [s * x^{s-1} + t * x^{t-1}].$$

Evaluating at x=1, $$q^{(1)}(1) = p^{(1)}(1) * (1^s + 1^t) + p(1) * [s * 1^{s-1} + t * 1^{t-1}],$$
$$= p^{(1)}(1) * (2) + p^{(0)}(1) * [s + t].$$

The $n^{th}$ moment of a polynomial $u(x)$ is $$u_n = u^{(n)}(1).$$

This may be very efficiently computed in linear time as the sum of the coefficients of the polynomial's $n^{th}$ derivative. The moments are related to more intuitive function statistics, such as the mean and variance:

$$E(u) = u_1/u_0, \text{ and}$$

$$E(u^2) = u_2/u_0 + u_1/u_0 - (u_1/u_0)^2.$$

Rewrite the above derivation as (easily computable) moment statistics:

$$q_1 = 2p_1 + (s+t)p_0,$$

or, $$q_1/p_0 = 2p_1/p_0 + s+t,$$

so:

$$s+t = q_1/p_0 - 2p_1/p_0,$$
$$= (q_1 - 2p_1)/p_0. \qquad (*)$$

Thus, given the hemizygous (or homozygous) distribution $p(x)$, and the sequencer data $q(x)$, if either s or t is known, then so is the other. When the position t of the larger allele is determined by identifying the peak of the largest PCR product in the locus region, this procedure will determine the location s of the smaller allele.

Step 5b. Computing an expression for the allele sum $s^2+t^2$. To extract second moments, compute the second derivative of the relation $$q(x)=p(x) * (x^s+x^t).$$

After simplification, this produces:

$$q^{(2)}(x) = p^{(2)}(x) * (x^s + x^t) + 2[p^{(1)}(x) * (sx^{s-1} + tx^{t-1})] +$$
$$p(x)[s(s-1)x^{s-2} + t(t-1)x^{t-2}].$$

Setting x=1 to calculate moments, and rearranging to group the constant, linear, and quadratic terms in s and t, yields the equality:

$$0=[2p_2-q_2]+(s+t)[2p_1-p_0]+(s^2+t^2)p_0.$$

Rearranging this equality gives the equivalence:

$$s^2+t^2=\{[q_2-2p_2]+(s+t)[p_0-2p_1]\}/p_0. \qquad (**)$$

Each right hand side term is directly or indirectly computable from moment properties of the data. For example, "s+t" is known via equation (*).

Step 5c. Computing an expression for the allele difference s−t.
From (s+t) given in (*), and $(s^2+t^2)$ given in (**), (s−t) is obtained as follows:

$$(s-t)^2 = s^2 - 2st + t^2$$
$$= s^2 + t^2 - 2st$$
$$= 2s^2 + 2t^2 - [s^2 + t^2 + 2st]$$
$$= 2(s^2 + t^2) - (s+t)^2.$$

This provides a closed form expression for s−t, as the square root of $2(s^2+t^2)-(s+t)^2$.

Step 5d. Computing the alleles s and t.
Combining s+t and s−t:

$$s=[(s+t)+(s-t)]/2, \text{ and}$$

$$t=[(s+t)-(s-t)]/2.$$

Thus, by taking zeroth, first, and second moments of the multiallelic sequence data $q(x)$, together with the known haplotype $p(x)$, the absolute positions of nucleotide repeat alleles s and t can be rapidly computed. Since computing the moments is just linear in the size of the data, the procedure is fast, and is asymptotically better than simple (and noise intolerant) quadratic time polynomial division; this speed advantage is useful in on-line real-time automated genotyping.

Referring to FIG. 1B, step 5' is for operating with Fourier domain techniques on the first set of electrical signals produced from the amplified material with a second set of electrical signals (described in step 6) corresponding to a response pattern of the location to produce a third set of clean electrical signals corresponding to the size and multiplicities of the unamplified material on the genome at the location.

The measured first set of electrical signals produced from the amplified material is corrupted by the response pattern of the location on the genome. The objective is to produce a third set of clean electrical signals corresponding to the size and multiplicities of the unamplified material on the genome at the location. This is done by operating on the first set of electrical signals, together with the second set of electrical signals detailed in step 6, using a program residing in the memory of the computer. In another preferred embodiment, this operation is Fourier domain deconvolution.

Fourier domain signal processing methods can be used for deconvolution and allele determination from stuttered PCR reactions. Fourier processing can readily recover more than two alleles from a sample, hence is highly applicable to population pooling studies. Here, each discrete time unit corresponds to a DNA size; this size measured in base pair (bp) units is observed on an electrophoretic gel trace. Using conventional signal processing notation, (1) the uncorrupted allele signal is the function $$u(t),$$

which maps each DNA size t into the number of alleles of that size present in the sample;

(2) the known PCR stutter pattern of a given genetic marker is $$r(t),$$

the response function describing the spatial appearance of one marker's stutter on the gel;

(3) the observed data from one or more alleles is the smeared signal $$s(t),$$

which is the appearance of the multiple superimposed alleles u(t) distorted by the stutter artifact r(t).

(4) That is:

$$s(t)=r(t) * u(t), \text{ where "*" denotes convolution,}$$

and, in the Fourier domain, $$S(f)=R(f)\, U(f),$$

where the capital letters denote the Fourier transforms of the signal functions. The objective is to genotype by determining the allele distribution u(t) from the observed data s(t), exploiting the known response function r(t).

In a preferred embodiment, u(t) is determined by steps of:

(1) measuring a first set of electrical signals s(t) produced from the amplified material, and computing its Fourier transform S(f), e.g., by applying a fast Fourier transform (FFT) procedure;

(2) retrieving a second set of electrical signals r(t) corresponding to a response pattern of the location, and computing its Fourier transform R(f);

(3) numerically dividing the function S(f) by the function R(f) at each frequency domain point to compute the function U(f);

(4) performing an inverse Fourier transformation on U(f) to compute the third set of clean electrical signals u(t) corresponding to the size and multiplicities of the unamplified material on the genome at the location.

When noise is problematic, a method such as Optimal (Wiener) Filtering with the (fast) Fourier transform is an alternative embodiment (D. F. Elliot and K. R. Rao, *Fast Transforms: Algorithms, Analyses, Applications*. New York: Academic Press, 1982; H. J. Nussbaumer, *Fast Fourier Transform and Convolution Algorithms*. New York: Springer-Verlag, 1982; A. Papoulis, *Signal Analysis*. New York: McGraw-Hill Book Company, 1977; L. R. Rabiner and B. Gold, *Theory and Application of Digital Signal Processing*. Englewood Cliffs, N.J.: Prentice-Hall, 1975), incorporated by reference. The following paragraph follows the method given in section 12.6 of Press (W. H. Press, B. P. Flannery, S. A. Teukolsky, and W. T. Vetterling, *Numerical Recipes in C: The Art of Scientific Computing*. Cambridge: Cambridge University Press, 1988), incorporated by reference.

When significant noise is present, the measured signal c(t) is further corrupted, and adds a component of noise n(t) to s(t):

$$c(t)=s(t)+n(t).$$

The optimal filter $\phi(t)$ or $\Phi(f)$ is applied to the measured signal c(t) or C(f), and is then deconvolved by the marker-dependent r(t) or R(f), to produce a signal v(t) or V(f) that is as close as possible to the uncorrupted allele signal u(t) or U(f). That is, the true signal U(f) is estimated (in the Fourier domain) by $$V(f)=C(f)\Phi(f)/R(f).$$

The "closeness" is least square minimization of v(t) and u(t), or, equivalently in the Fourier domain, V(f) and U(f). The optimal filter $\Phi(f)$ is given by $$\Phi(f)=|S(f)|^2/(|S(f)|^2+|N(f)|^2),$$

where N(f) is the Fourier transform of the noise function n(t). N(f) can be determined from calibration data in the absence of allele signal, or by the straightforward extrapolation scheme described in pp. 434–437 and FIG. 1 2.6.1 of (W. H. Press, B. P. Flannery, S. A. Teukolsky, and W. T. Vetterling, *Numerical Recipes in C: The Art of Scientific Computing*. Cambridge: Cambridge University Press, 1988). Inverse Fourier transformation of the computed V(f) produces v(t), which is the optimal estimate of the allele distribution u(t).

Referring to FIG. 1B, step 5" is for operating with matrix processing techniques on the first set of electrical signals produced from the amplified material with a second set of electrical signals (described in step 6) corresponding to a response pattern of the location to produce a third set of clean electrical signals corresponding to the size and multiplicities of the unamplified material on the genome at the location.

For some markers, the PCR stutter pattern may show considerable variation with allele size. This variation is generally smooth, with close sizes showing very similar patterns. Thus, in deconvolving two closely spaced alleles (e.g., in the case of superimposed heterozygote alleles with a single individual's DNA), linear shift-invariant deconvolution methods that employ only one pattern in the deconvolution process (such as the described moment-based and Fourier-based methods) are quite robust approximations. However, for these and more complex problems (e.g., genotyping pooled DNA samples), a more refined (non-shift-invariant) deconvolution method that accounts for this allelic stutter pattern variation may be preferable.

A more refined approach to the data employs a set of stutter patterns for each marker. This set provides a continuum of stutter patterns that vary with the allele size. (This set may be comprised of several such size-dependent subsets, with one subset for each unique continuum of stutter patterns of the marker.) This set is experimentally derived by observing the stutter patterns under replicatable PCR conditions at different allele sizes, and possibly interpolating at allele sizes for which experimental data is not available. These measured and inferred patterns are preferably normalized, and stored in a table.

Matrix processing techniques can be used to model the non-shift-invariant convolution process, and to perform a wide variety of deconvolution tasks that exploit the continuum of stutter pattern variation. One may write the convolution process for a given marker under relatively fixed PCR conditions as the matrix equation $$y = A\,x,$$

where:
- (x) the vector x is the actual input distribution of alleles, where each entry of x corresponds to an allele size, and the entry's value corresponds to the number of alleles present of that size;
- (y) the vector y is the measured output distribution (e.g., as observed on an electrophoretic gel), where each entry of y corresponds to an allele size, and the entry's value corresponds to a measured concentration of DNA at that size;
- (A) the columns of matrix A contain the allele-size-dependent stutter patterns, where each column corresponds to the actual input allele sizes, and each row corresponds to the output measured output DNA concentrations. The entries of A are preferably normalized to a common total DNA concentration value in each column.

Deconvolution processing in this model is done by inverting the linear equations described by A, to compute the actual x allele vector from the observed y data vector. Since A is generally not a square matrix, this inversion operation is done by computing an x which minimizes error. In the preferred embodiment, this error is computed as the least squares deviation of the observed data vector y from the estimated vector Ax. The search for the best x can be done by direct enumeration and evaluation of all feasible discrete allele vectors, or by numerical methods such as singular value decomposition (SVD) which numerically "invert" the nonsquare matrix to determine a continuous-valued approximation to x (W. H. Press, B. P. Flannery, S. A. Teukolsky, and W. T. Vetterling, *Numerical Recipes in C: The Art of Scientific Computing*. Cambridge: Cambridge University Press, 1988), incorporated by reference. Note that the direct enumeration method is computationally feasible, since there are only a quadratic number of feasible allele pair vectors.

When the columns of A are unit shifted vectors having the identical values, the matrix model reduces to the linear shift-invariant case. For example, the stutter pattern vector <1.0, 0.5, 0.25, 0.125> replicated with unit shifting in each successive column of the matrix would be written as:

| 1.0000 | 0 | 0 | 0 | 0 |
|---|---|---|---|---|
| 0.5000 | 1.0000 | 0 | 0 | 0 |
| 0.2500 | 0.5000 | 1.0000 | 0 | 0 |
| 0.1250 | 0.2500 | 0.5000 | 1.0000 | 0 |
| 0 | 0.1250 | 0.2500 | 0.5000 | 1.0000 |
| 0 | 0 | 0.1250 | 0.2500 | 0.5000 |
| 0 | 0 | 0 | 0.1250 | 0.2500 |
| 0 | 0 | 0 | 0 | 0.1250 |

More generally, the columns of A provide a continuum of response stutter pattern vectors. An illustrative example that will be used throughout is the matrix A, whose columns give the stutter pattern response to a unit input for each allele size.

A =

| 1.0000 | 0 | 0 | 0 | 0 |
|---|---|---|---|---|
| 0.5000 | 1.0000 | 0 | 0 | 0 |
| 0.2500 | 0.6000 | 1.0000 | 0 | 0 |
| 0.1250 | 0.3000 | 0.7000 | 1.0000 | 0 |
| 0 | 0.1500 | 0.3500 | 0.8000 | 1.0000 |
| 0 | 0 | 0.1600 | 0.4000 | 0.9000 |
| 0 | 0 | 0 | 0.2000 | 0.4500 |
| 0 | 0 | 0 | 0 | 0.2200 |

In this example matrix A, the columns correspond to five input allele sizes (say, from left to right, 114bp, 112bp, 110bp, 108bp, and 106bp), while the rows correspond to eight output allele sizes (say, from top to bottom, 114bp, 112bp, 110bp, 108bp, 106bp, 104bp, 102bp, and 100bp).

Given this example A, suppose an individual's genotype had the alleles 112bp, and 108bp present. Then the input x could be written as the column vector <0 1 0 1 0>, where a "1" designates that one unit of the allele is present, while a "0" indicates the allele's absence. PCR amplification of this genotype would result in a signal corresponding to superposition of the PCR-stutter distorted two alleles. PCR amplification of the 112bp allele would produce DNA concentrations of 112bp, along with smaller stutter fragments; this is precisely the second (i.e., 112bp) column of A, or the matrix/vector product:

$$A <0\ 1\ 0\ 0\ 0> = <0,\ 1.0,\ 0.6,\ 0.3,\ 0.15,\ 0,\ 0,\ 0>.$$

PCR amplification of the 108 bp allele would produce DNA concentrations of 108bp, along with smaller stutter fragments; this is precisely the fourth (i.e., 108bp) column of A, or the matrix/vector product:

$$A <0\ 0\ 0\ 1\ 0> = <0,\ 0,\ 1.0,\ 0.8,\ 0.4,\ 0.2,\ 0>.$$

Superposition of these two alleles will produce the sum of their DNA concentration response patterns, or the matrix/vector product:

$$A <0\ 1\ 0\ 1\ 0> = <0,\ 1.0,\ 0.6,\ 1.3,\ 0.95,\ 0.4,\ 0.2,\ 0>.$$

Deconvolution in this example is done by error minimization with respect to the allele-size dependent pattern response matrix A.

(1) Using a discrete method, enumeration of all feasible vectors x whose entries are positive integers and whose entries sum preferably does not exceed 2, the mimimal least square error is obtained with the allele vector <0 1 0 1 0>. When no noise is present, $$\mathrm{norm}(<0, 1.0, 0.6, 1.3, 0.95, 0.4, 0.2, 0> - A <0\ 1\ 0\ 1\ 0>) = 0.0,$$

where "norm" denotes the L2 (sum of squared deviations) norm. Since the remaining feasible solutions have errors in the range [1.1771, 2.6069], the correct solution having minimal error 0.0 was found.

(2) Using this discrete method when random noise is present, say at a +/−10% level, one may simulate an observed y vector of

<0.0027 1.0182 0.6692 1.2824 1.0183 0.3539 0.1831 0.0075>, and the error of the true x solution <0 1 0 1 0> is 0.1121. Since the remaining feasible solutions have errors in the range [1.1341, 2.6240], the correct solution having minimal error 0.1121 was found.

(3) Using a continuous nonsquare matrix inversion method, SVD inversion of A with the data vector y when no noise is present recovers the genotype vector x=<0 1 0 1 0>.

(4) Using the continuous SVD method with the (simulated) noise corrupted data vector y used in (2), the computed allele vector x is:

<−0.0014, 1.0233, 0.0526, 0.9593, 0.0205>, which (e.g., by rounding) produces the correct genotype vector <0 1 0 1 0>.

One reason for the robustness of the SVD solution is that the pattern matrix A has a form similar to an identity matrix, as seen by A's eigenvalues 2.0198, 1.4831, 1.0302, 0.7811, and 0.6237. Since the eigenvalues for the pattern matrices A of markers tend to have eigenvalues far from 0.0, the solutions are robust and stable.

Pooled DNA experiments are very useful with genomic analysis methods based on affected pedigree members (D. E. Weeks and K. Lange, "The affected pedigree member method of linkage analysis," *Am. J. Hum. Genet.*, vol. 42, pp. 315–326, 1988; D. E. Weeks and K. Lange, "A multilocus extension of the affected-pedigree-member method of linkage analysis," *Am. J. Hum. Genet.*, vol. 50, pp. 859–868, 1992), incorporated by reference, or sib-pairs (L. Penrose, Ann. Eugenics, vol. 18, pp. 120–124, 1953), incorporated by reference, and can reduce the number of required experiments. In these experiments, equimolar (or other known) concentrations of DNA from more than one individual are pooled together for readout. This DNA pooling is preferably done prior to the PCR amplification of the sample, but may be done following the amplification step. With marker-specific PCR stutter artifact, a reproducible data vector y is generated, but the corresponding allele vector x is not known. By applying a deconvolution process that exploits the stutter pattern, the allele vector x can be determined. In the preferred embodiment, this determination of the pooled allele distribution is made using matrix processing that can account for allele-size dependencies in the stutter patterns.

As an example, again use the stutter pattern matrix A, and introduce the six actual individual marker genotypes:

<0 1 0 1 0>, <1 0 0 1 0>, <1 1 0 0 0>, <1 0 0 0 1>, <0 0 1 1 0>, <0 0 0 2 0>.

The actual allele vector x is a pooling of these unknown genotypes, and sums their components:

<3 2 1 5 1>.

In the absence of noise, the measured vector y=Ax would be

<3.0, 3.5, 2.95, 6.675, 5.65, 3.06, 1.45, 0.22>, and, with +/−10% noise, the vector y is

<2.9936, 3.4574, 2.8857, 6.6057, 5.6643, 3.1205, 1.3566, 0.2269>.

The pooled allele vector x can be determined from the measured noisy vector y by deconvolving with the known stutter patterns. In the preferred embodiment, SVD of the data vector y with respect to the pattern matrix A estimates the allele distribution vector x as:

<2.9931, 1.9569, 0.9707, 4.9699, 1.0421>, which yields (e.g., with rounding) the actual allele vector x

<3 2 1 5 1>.

Referring to FIG. 1B, step 6 is for providing a second set of electrical signals corresponding to a response pattern of the location that is used when (see steps 5 and 5') operating on the first set of electrical signals produced from the amplified material to produce a third set of clean electrical signals corresponding to the size and multiplicities of the unamplified material on the genome at the location.

A second set of electrical signals corresponding to a response pattern of the location on a genome is used in recovering the clean third set of electrical signals from the corrupted first set of electrical signals. This second set of electrical signals is generated by deconvolution of routine first sets of electrical signals, as described above, or by a simple laboratory assay, as described next, and is stored in the memory of a computer.

The genotype of an individual at an STR can be determined without typing relatives of that individual. This is because the stutter pattern of an STR locus is largely independent of the particular individuals or families, and depends primarily on the locus, the PCR conditions, and the allele size. Thus, by building and using a library of PCR stutter patterns, all STR loci can be genotyped by the described deconvolution method. Specifically, this includes all STRs on autosomes or sex chromosomes, for DNA from single individuals or from pooled individual samples.

In the preferred embodiment, each locus pattern in the STR library is determined by PCR amplification and subsequent quantitative analysis of the size separation distribution. There are three cases, hemizygote/homozygote, distinct heterozygote, or superimposed heterozygote. When an individual is found whose genotype assay is classified into one of the first two cases, the observed distinct allele pattern can be directly stored in the library. When only superimposed heterozygotes are found, the following is done:

(a) A small finite number of candidate solution allele pairs (s,t) that include the correct allele pair are made, based on the localized region of the assay.

(b) Each allele pair candidate solution (s,t) is used to deconvolve the observed fit. This is done by respecting the relationship $p(x) = q(x)/(x^2+x^t)$ to compute a candidate $p(x)$.

(c) The best allele candidate solution (s,t) which fits the data, in accordance with the allele superposition principle, computes the stutter patterns $p(x)$ of the locus.

(d) This determination is preferentially repeated with additional individuals. It is preferrable for the deconvolution determination that these individuals be related. Further, the observed data or resulting stutter patterns are preferrentially combined to reduce noise.

(e) The resulting allele size dependent stutter patterns $p(x)$ of the locus are stored in the STR library.

In an alternative embodiment, individual haploid chromosomes are obtained by microdissection, with an optional subsequent cloning step. PCR of single chromosomes (or their clones) produces a single allele stutter pattern. These patterns $p(x)$ are then recorded in the library.

In a preferred embodiment for determining a marker's allele-size dependent PCR stutter patterns, matrix processing is used. With A as the stutter pattern matrix introduced in step 5", the allele-size dependent PCR stutter patterns correspond to the columns of matrix A, and the task is to determine this matrix A. Since y=Ax, from a known set of (column) reference genotype vectors X used to probe A, a corresponding set of experimentally observed data (column) vectors Y can be generated. Note that each set of column vectors (i.e., X and Y) is a matrix. This extends the stutter pattern matrix relation to $$Y=AX,$$

where Y, A, and X are matrices. By matrix division (i.e., numerical solution by the generally non-square matrix X using least square minimization of the under- or over-determined system), the relation $$A=Y/X$$

allows the determination of the stutter pattern matrix A.

In one preferred embodiment for matrix processing determination of the stutter pattern matrix A in step 6, each probing column vector in X represents one individual's genotype, i.e., a known pair of alleles. As an illustrative example of determining A using individual allele pair probes, let A be the actual, but unknown, stutter matrix to be determined. The matrix X of column probes is constructed from six samples of known genotype, with each known allele pair represented in one matrix column. For example,

| X = | | | | | |
|---|---|---|---|---|---|
| 1 | 1 | 0 | 0 | 0 | 1 |
| 1 | 0 | 1 | 1 | 0 | 0 |
| 0 | 1 | 1 | 0 | 1 | 0 |
| 0 | 0 | 0 | 1 | 0 | 0 |
| 0 | 0 | 0 | 0 | 1 | 1 |

Performing PCR amplification experiments for each sample, and determining the size and DNA concentrations for each, the result $Y=AX$ can be experimentally determined. Using the example A and X,

| Y = | | | | | |
|---|---|---|---|---|---|
| 1.0000 | 1.0000 | 0 | 0 | 0 | 1.0000 |
| 1.5000 | 0.5000 | 1.0000 | 1.0000 | 0 | 0.5000 |
| 0.8500 | 1.2500 | 1.6000 | 0.6000 | 1.0000 | 0.2500 |
| 0.4250 | 0.8250 | 1.0000 | 1.3000 | 0.7000 | 0.1250 |
| 0.1500 | 0.3500 | 0.5000 | 0.9500 | 1.3500 | 1.0000 |
| 0 | 0.1600 | 0.1600 | 0.4000 | 1.0600 | 0.9000 |
| 0 | 0 | 0 | 0.2000 | 0.4500 | 0.4500 |
| 0 | 0 | 0 | 0 | 0.2200 | 0.2200 |

The stutter pattern matrix A is estimated by solving the linear system; this can be done using least squares minimization, or by using the matrix division utility in a standard mathematics package (MatLab program and manual, The Mathworks, Natick, Mass.), incorporated by reference. Without noise added, A is exactly recovered. Adding +/−10% noise to Y gives:

| Y = | | | | | |
|---|---|---|---|---|---|
| 0.9579 | 1.0459 | 0.0050 | 0.0833 | −0.0108 | 0.9423 |
| 1.5075 | 0.5739 | 0.9927 | 1.0732 | −0.0369 | 0.5998 |
| 0.8529 | 1.2931 | 1.5130 | 0.6780 | 1.0029 | 0.1807 |
| 0.3457 | 0.8851 | 1.0427 | 1.3088 | 0.7763 | 0.1511 |
| 0.1328 | 0.3913 | 0.4978 | 0.8778 | 1.3379 | 1.0233 |
| 0.0153 | 0.2083 | 0.1935 | 0.3901 | 1.0535 | 0.8001 |
| 0.0753 | −0.0962 | 0.0364 | 0.2979 | 0.5113 | 0.3502 |
| −0.0120 | 0.0772 | −0.0601 | −0.0569 | 0.1930 | 0.2747 | for which matrix division estimates a stutter pattern matrix A of:

| Estimated A = | | | | |
|---|---|---|---|---|
| 0.9995 | −0.0415 | 0.0465 | 0.1249 | −0.0572 |
| 0.5748 | 0.9631 | −0.0009 | 0.1100 | −0.0054 |
| 0.2760 | 0.5364 | 1.0172 | 0.1416 | −0.0547 |
| 0.1120 | 0.2516 | 0.7731 | 1.0572 | 0.0211 |
| 0.0257 | 0.1196 | 0.3656 | 0.7582 | 0.9850 |
| −0.0037 | 0.0003 | 0.2121 | 0.3898 | 0.8226 |
| −0.0787 | 0.1040 | −0.0175 | 0.1939 | 0.4788 |
| 0.0710 | −0.0746 | 0.0062 | 0.0178 | 0.1952 |

When such estimated A pattern matrices are combined with noise corrupted data vectors y, accurate genotypes x are computed.

In another preferred embodiment for matrix processing determination of the stutter pattern matrix A in step 6, each probing column of X is constructed from pooled individual DNAs having known genotypes. This embodiment enables customization of the matrix X, and may reduce the number of required probing experiments. In one illustrative example of using pooled DNA genotypes to determine matrix A, each column probe is pooled from three individuals, and contains six alleles.

| X = | | | | | |
|---|---|---|---|---|---|
| 1 | 1 | 0 | 0 | 1 | 0 |
| 2 | 0 | 1 | 0 | 1 | 2 |
| 2 | 2 | 2 | 1 | 1 | 0 |
| 1 | 0 | 0 | 3 | 1 | 2 |
| 0 | 3 | 3 | 2 | 2 | 2 |

The assayed size distribution for each experiment $Y=AX$ is

| Y = | | | | | |
|---|---|---|---|---|---|
| 1.0000 | 1.0000 | 0 | 0 | 1.0000 | 0 |
| 2.5000 | 0.5000 | 1.0000 | 0 | 1.5000 | 2.0000 |
| 3.4500 | 2.2500 | 2.6000 | 1.0000 | 1.8500 | 1.2000 |
| 3.1250 | 1.5250 | 1.7000 | 3.7000 | 2.1250 | 2.6000 |
| 1.8000 | 3.7000 | 3.8500 | 4.7500 | 3.3000 | 3.9000 |
| 0.7200 | 3.0200 | 3.0200 | 3.1600 | 2.3600 | 2.6000 |
| 0.2000 | 1.3500 | 1.3500 | 1.5000 | 1.1000 | 1.3000 |
| 0 | 0.6600 | 0.6600 | 0.4400 | 0.4400 | 0.4400 |

Solving the linear system of equations by least squares minimization in MatLab via the expression "Y/X" without added noise exactly computes A. When noise is added, the result is robustly close to A.

| Estimate A = | | | | |
|---|---|---|---|---|
| 1.0369 | 0.0127 | 0.0349 | 0.0444 | −0.0054 |
| 0.4768 | 1.0603 | 0.0320 | −0.0045 | 0.0127 |
| 0.2839 | 0.6420 | 1.0175 | −0.0003 | −0.0036 |
| 0.1227 | 0.3189 | 0.7364 | 0.9846 | 0.0106 |
| 0.0135 | 0.1859 | 0.3043 | 0.7950 | 1.0494 |
| 0.0553 | −0.0073 | 0.1715 | 0.4437 | 0.9034 |
| 0.1308 | −0.0170 | −0.0010 | 0.2128 | 0.4601 |
| 0.0507 | 0.0452 | −0.0558 | −0.0158 | 0.2767 |

To genotype an individual's STR locus (particularly in the superimposed heterozygote case), the stutter pattern of the locus is retrieved from the library. This pattern, possibly dependent on allele size, is combined with the individual's locus data (using the allele deconvolution methods detailed in steps 5, 5', and 5" of FIG. 1B) to determine the genotype.

Figure 5:
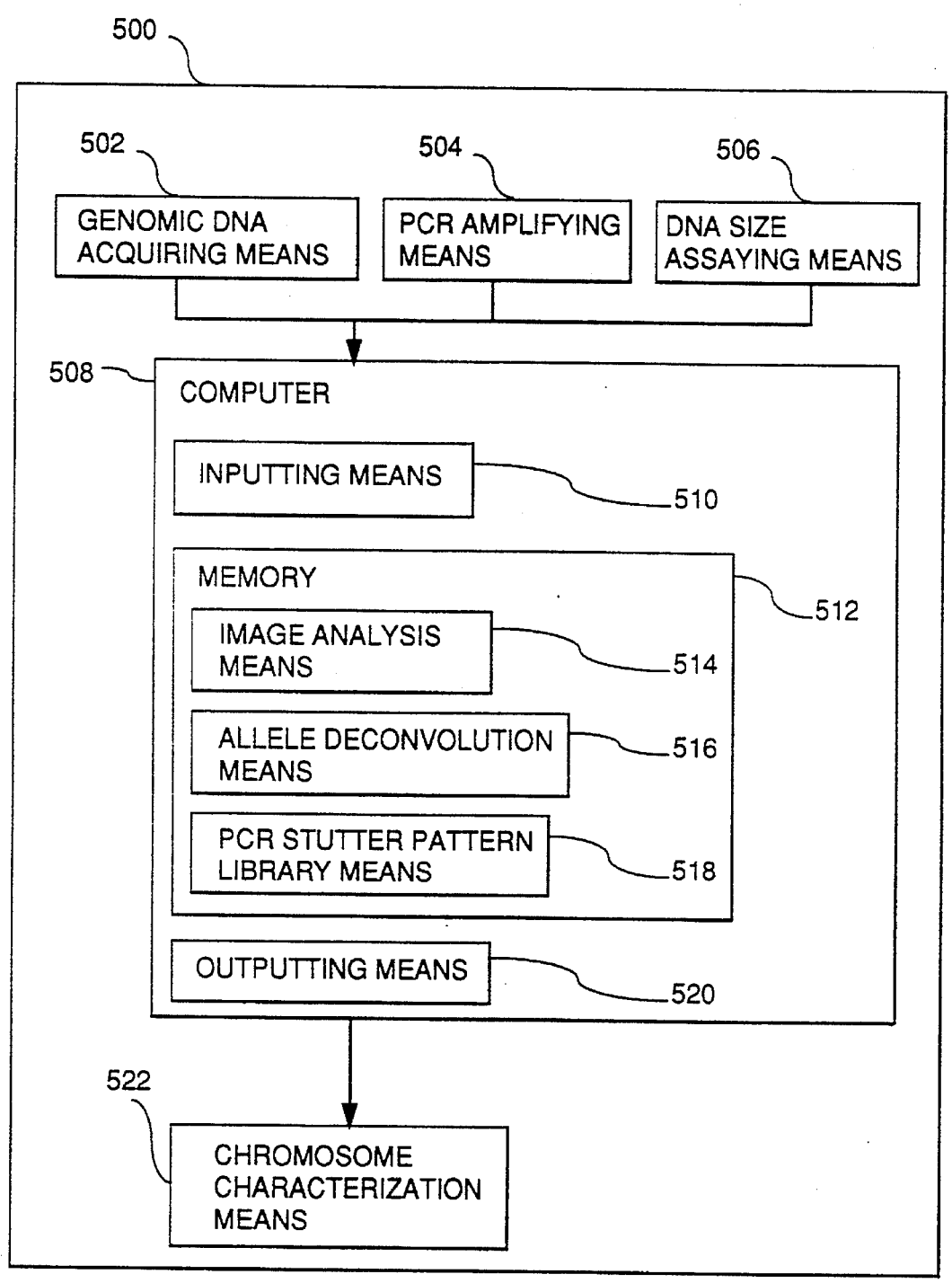
FIG. 5 is a schematic representation of a system for genotyping polymorphic genetic loci.

Referring to FIG. 5, a system for genotyping polymorphic genetic loci comprised of a computer device with memory and an inputting means is described.

Referring now to the drawings wherein like reference numerals refer to similar or identical parts throughout the several views, and more specifically to FIG. 5 thereof, there is shown a schematic representation of a system 500 for genotyping polymorphic genetic loci. The system 500 comprises a means 502 for obtaining nucleic acid material from a genome. The system 500 comprises a means 504 for PCR amplification of one or more STR loci of the acquired genomic DNA. The system 500 also comprises a means 506 for assaying the differential sizes and concentrations of the PCR amplified DNA. In the preferred embodiment, means 508 is effected by gel electrophoresis and the formation of an image.

The system 500 comprises a computer 508 with an inputting means 510, a memory 512, and an outputting means 520. The assayed differential DNA sizes and concentrations are entered into the computer 508 via the inputting means 510. The system 500 comprises a means 514 for analyzing images into DNA size and concentration features at locations on the image, thereby converting the assayed amplified material into a first set of electrical signals corresponding to size and concentration of the amplified material at the location. The system 500 also comprises a means 516 for deconvolving the DNA size and concentration features into their underlying genotypes, thereby removing PCR stutter artifact. This deconvolving means 516 may make use of a means 518 (that uses the memory 512) for constructing, recording, and retrieving PCR stutter patterns. More generally, the means 516 is for operating on the first set of electrical signals produced from the amplified material with a second set of electrical signals corresponding to a response pattern of the location to produce a third set of clean electrical signals corresponding to the size and multiplicities of the unamplified material on the genome at the location.

The system 500 comprises an outputting means 520 that makes the computed genotypes available for further processing; these genotypes are derived from the third set of clean electrical signals corresponding to the size and multiplicities of the unamplified material on the genome at the location. The system 500 may optionally comprise a means 522 for further characterizing chromosomes from the outputted genotypes. Such means 522 include genetic diagnosis, the construction or use of genetic maps, the positional cloning of genes, genetic monitoring of cancerous materials, genetic fingerprinting, and the genotyping of populations.

(2) A system for diagnosing genetic disease.

Referring to FIG. 6, step 1 determines genotypes of related individuals.

This is done using the method of FIG. 1B.

Referring to FIG. 6, step 2 sets chromosome phase by graph propagation, deductive methods, or likelihood analysis.

For linkage-based molecular diagnostics, it is often useful to know the phase of the chromosomes. The example of DMD is presented as one preferred embodiment.

Once the genotypes have been determined for a DMD pedigree, phase is easily set on the X chromosome. This is done by treating the pedigree as a graph, where the nodes are the individuals, and the links are the inheritance paths between them. Starting from a male descendant (e.g., the proband), the neighboring nodes that are one inheritance link away (whether child or parent) are explored. Individual haplotypes are locally determined from haplotyped neighbors, as follows:

* Male individuals are given the haplotype of their hemizygotic genotype.
* Female individuals are set from a male neighbor by assigning one haplotype to the male's haplotype, and assigning the second haplotype as the difference at each marker of the individual's genotype and the male haplotype.
* Female individuals are set from a haplotyped female neighbor by first determining which (if either) of the neighbor's haplotypes is contained within the individual's genotype. This haplotype becomes the first haplotype of the individual, and the second haplotype is obtained as the difference at each marker of the individual's genotype and the first haplotype.

Other local computations can be done when visiting each node, such as assessing consistency. Since the graph traversal only propagates to unhaplotyped neighbors, the process terminates when all individuals have been consistently haplotyped.

Independent graph propagations from each male descendant are done. The propagation locally terminates at an individual when a parent-child haplotype inconsistency is detected. This early termination can suggest where recombination (or other events) occur in the pedigree, and how to correct for their occurrence.

An example of setting phase from the allele data is illustrated with female individual D and male proband A from Family #40. The genotype of D across the four dystrophin markers

5 DYS-II, STR-45, STR-49, 3-CA is the allele sequence (277, 215), (171, 175), (233, 264), (131, 131).

A's haplotype is 207, 171, 233, 131.

Figure 7:
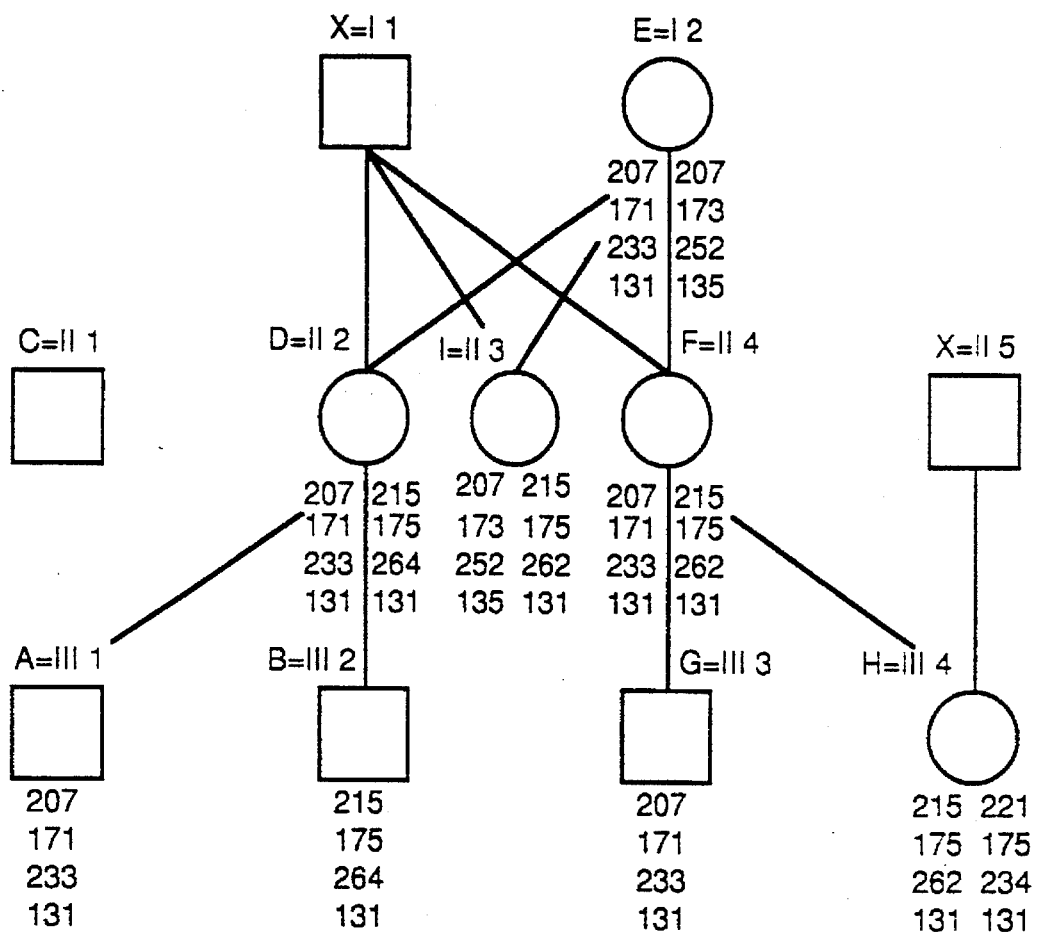
FIG. 7 shows the setting of phase in the inheritance graph. The links between the individuals in Family #40 show the X-chromosome inheritance paths between parents and children. These links are traversed to generate the vertical, in phase, haplotypes shown. This is done by applying the haplotyping rules when graph nodes (i.e., individuals) are reached in the graph traversal. This diagram was drawn by the graphical display component of the system.

Extracting this haplotype from D's genotype leaves 215, 175, 264, 131;

These two sequences describe D's two haplotypes. FIG. 7 shows the complete haplotyping for example Family #40 using this method for setting phase.

For autosomal chromosomes, phase is set in the preferred embodiment by likelihood methods (G. M. Lathrop and J.-M. Lalouel, "Efficient computations in multilocus linkage analysis," *Amer. J. Hum. Genet.*, vol. 42, pp. 498–505, 1988; J. Ott, *Analysis of Human Genetic Linkage, Revised Edition.* Baltimore, Md.: The Johns Hopkins University Press, 1991), incorporated by reference, or by deductive analysis (E. M. Wijsman, "A Deductive Method of Haplotype Analysis in Pedigrees," *Am. J Hum. Genet*, vol 41, pp. 356–373, 1987), incorporated by reference.

Referring to FIG. 6, step 3 determines the phenotypic risk of disease for the individuals.

The phenotype is inferred by comparing the proband's signature haplotype with the haplotypes of other related individuals in the pedigree. The multiple informative markers assures that, with high probability, identity-by-state of the multiple markers implies identity-by-descent. Thus, an identical signature at a related individual in the pedigree implies a shared chromosomal segment, including the diseased gene region(s). For example, with X-linked disorders, males sharing an affected proband's signature are presumed to be affected, whereas females sharing this signature are presumed carriers. Once the entire pedigree has been haplotyped, the affected, unaffected, and carrier (with X-linked disease) individuals are inferred. If no recombination events are found, then the disease gene haplotype of the proband serves as a signature that indicates an affected disease gene. Related persons with the disease gene haplotype are thus inferred to have carry the disease gene. The phenotypic status of disease gene carriers depends on the mode of genetic transmission: with purely recessive disorders, one disease gene dose causes disease, whereas with purely dominant disorders, all chromosomes must be affected. With variable expressivity, variable penetrance, and multigenic or multifactorial disorders, having the disease gene does not necessarily imply phenotypic disease.

Phenotypes are then determined. In Family #40, for example, proband A's allele signature at the four markers

5 DYS-II, STR-45, STR-49, 3-CA is the allele sequence 207, 171, 233, 131.

Figure 8:
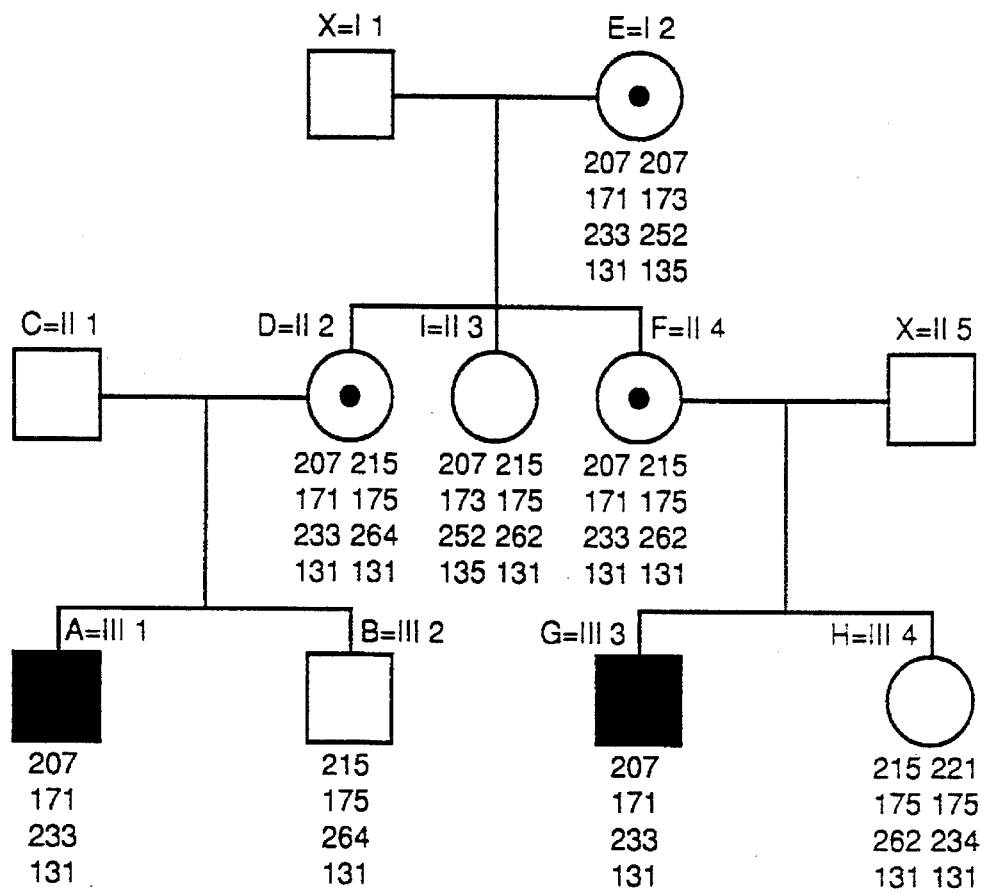
FIG. 8 shows phenotypic identification of individuals having the at-risk haplotype. All individuals who share a chromosomal haplotype with proband A are inferred to carry the disease gene. A's haplotype is the allele sequence <207,171,233,131>. Male G has this haplotype, and is presumed to be affected. Females D, E, and F have this haplotype on one of their X chromosomes, and are inferred to be carriers. This diagram was drawn by the graphical display component of the system.

All individuals in Family #40 sharing this sequence on one of their haplotyped chromosomes are presumed to also share the affected proband's disease gene. Thus, individual G is inferred to be another affected male, and the individuals D, E, and F are inferred to be carrier females. The phenotyped pedigree is shown in FIG. 8.

In non-X-linked disorders, the multiple linked markers enable phenotype determination via Bayesian analysis. This is done using conventional (I.D. Young, *Introduction to Risk Calculation in Genetic Counselling*. Oxford: Oxford University Press, 1991), incorporated by reference, or rule-based (D. K. Pathak and M. W. Perlin, "Automatic Computation of Genetic Risk," in *Proceedings of the Tenth Conference on Artificial Intelligence for Applications*, San Antonio, Tex., 1994, pp. 164–170), incorporated by reference, techniques.

Referring to FIG. 6, step 4 presents the results.

The results of the molecular diagnostics analysis is then presented in a usable form. In one preferred embodiment, a graphical computer interface is used to present the pedigree, annotated with the results of the genetics computations. A preferred implementation is to use object-oriented programming techniques, and to associate an object with each individual in the pedigree, and an object with each link between individuals in the pedigree. These objects are used to access the individual-specific data, to perform the inter-individual graph processing, and to execute all display functionality by having objects display representations of themselves in the appropriate contexts. Such display representations include graphical objects (e.g., circles, squares, and lines), and textual annotations.

(3) A system for constructing genetic maps.

A system for constructing genetic linkage maps comprising the steps of:

1. Determining genotypes from STR loci using the method of FIG. 1B.
2. Entering data and pedigree information into a computer device with memory. This data entry can be done manually, or automatically, as in (D. K. Pathak and M. W. Perlin, "Intelligent Interpretation of PCR Products in 1D Gels for Automatic Molecular Diagnostics," in *Seventh Annual IEEE Symposium on Computer-based Medical Systems*, Winston-Salem, N.C., 1994), incorporated by reference.
3a. Running the LINKAGE program to build a genetic map (G. M. Lathrop and J. -M. Lalouel, "Efficient computations in multilocus linkage analysis," *Amer. J. Hum. Genet.*, vol 42, pp. 498–505, 1988; J. Ott, *Analysis of Human Genetic Linkage, Revised Edition*. Baltimore, Md.: The Johns Hopkins University Press, 1991), incorporated by reference.
3b. In an alternative embodiment, applying the automated MultiMap program (T. C. Matise, M. W. Perlin, and A. Chakravarti, "Automated construction of genetic linkage maps using an expert system (MultiMap): application to 1268 human microsatellite markers," *Nature Genetics*, vol. 6, no. 4, pp. 384–390, 1994; P. Green, "Rapid construction of multilocus genetic linkage maps. I. Maximum likelihood estimation," Department of Genetics Washington University School of Medicine, draft manuscript, 1988.), incorporated by reference, to the data.

(4) A system for genetically localizing genetic traits.

A system for localizing genetic traits on a genome map comprising the steps of:

1. Determining genotypes from STR loci using the method of FIG. 1B.
2. Entering data and pedigree information into a computer device with memory. This data entry can be done manually, or automatically, as in (D. K. Pathak and M. W. Perlin, "Intelligent Interpretation of PCR Products in 1D Gels for Automatic Molecular Diagnostics," in *Seventh Annual IEEE Symposium on Computer-based Medical Systems*, Winston-Salem, N.C., 1994), incorporated by reference.
3a. Running the LINKAGE program to localize traits on the genetic map (G. M. Lathrop and J. -M. Lalouel, "Efficient computations in multilocus linkage analysis," *Amer. J. Hum. Genet.*, vol. 42, pp. 498–505, 1988), incorporated by reference.
3b. In an alternative embodiment, applying the automated MultiMap program (T. C. Matise, M. W. Perlin, and A. Chakravarti, "Automated construction of genetic linkage maps using an expert system (MultiMap): application to 1268 human microsatellite markers," *Nature Genetics*, vol. 6, no. 4, pp. 384–390, 1994), incorporated by reference, to the data.
3c. In another alternative embodiment, using linked genetic markers to determine location (E. S. Lander and D. Botstein, "Mapping Complex Genetic Traits in Humans: New Methods Using a Complete RFLP Linkage Map," in *Cold Spring Harbor Symposia on Quantitative Biology*, vol. LI, Cold Spring Harbor, Cold Spring Harbor Laboratory, 1986, pp. 49–62), incorporated by reference. Elaborations and variations of this approach, with appropriate statistics and genotype comparison mechanisms, include (L. Penrose, *Ann. Eugenics*, vol. 18, pp. 120–124, 1953; N. E. Morton, *Am. J. Hum. Genet.*, vol. 35, pp. 201–213, 1983; N. Risch, *Am. J. Hum. Genet.*, vol. 40, pp. 1–14, 1987; E. Lander and D. Botstein, *Genetics*, vol. 121, pp. 185–199, 1989; N. Risch, "Linkage strategies for genetically complex traits," in three parts, *Am. J. Hum. Genet.*, vol. 46, pp. 222–253, 1990; N. Risch, *Genet. Epidemiol.*, vol. 7, pp. 3–16, 1990; N. Risch, *Am. J. Hum. Genet.*, vol. 48, pp. 1058–1064, 1991; P. Holmans, *Am. J. Hum. Genet.*, vol. 52, pp. 362–374, 1993; N. Risch, S. Ghosh, and J. A. Todd, *Am. J. Hum. Genet.*, vol. 53, pp. 702–714, 1993; R. C. Elston, in *Genetic Approaches to Mental Disorders*, E. S. Gershon and C. R. Cloninger, ed. Washington D.C.: American Psychiatric Press, 1994, pp. 3–21), incorporated by reference.

Another approach based on linked genetic markers is Inner Product Mapping (IPM) superposition of alleles. For a (small) chromosomal region that includes the causative gene, termed the concordant region, all affected/carrier individuals in a pedigree will share (roughly) identical chromosomal material, whereas each unaffected/noncarrier individual will have nonidentical material. A highly informative genetic marker that lies within the concordant region will exhibit complete concordance, markers that lie near the concordant region will show high (though incomplete) concordance, and markers far from the concordant region will have random concordance. From a linkage analysis perspective, fully haplotyped chromosomes for an X-linked trait can be viewed as radiation hybrids (D. R. Cox, M. Burmeister, E. R. Price, S. Kim, and R. M. Myers, "Radiation hybrid mapping: a somatic cell genetic method for constructing high-resolution maps of mammalian chromosomes," *Science*, vol. 250, pp. 245–250, 1990), incorporated by reference. Inner product mapping (IPM) (M. W. Perlin and A. Chakravarti, "Efficient Construction of High-Resolution Physical Maps from Yeast Artificial Chromosomes using Radiation Hybrids: Inner Product Mapping," *Genomics*, vol. 18, pp. 283–289, 1993), incorporated by reference, is a physical mapping method for localizing DNA probes based on concordance of radiation hybrid probings which can be adapted to localizing X-linked disease genes on a genetic map.

With fully informative genetic markers, identity-by-state (IBS) analysis uses allele information directly from the genotyping data. For haplotyped X-linked traits, an individual is concordant for a marker allele when either the individual is phenotypically affected/carrier and shares the allele with the affected/carrier founder, or the individual is phenotypically unaffected/noncarrier and does not share the allele with the affected/carrier founder. For every marker, IPM-concordance analyzes each founder allele separately, forming the sum of concordant individuals in the pedigree; the greatest sum is the concordance value of the marker. When genetic markers are not fully informative, an identity-by-descent (IBD) analysis of a marker allele weights each individual in the sum by the probability that the allele was inherited from the founder.

When a fully concordant value is detected at a candidate marker, the marker's significance for linkage can be measured by examining the concordance at nearby linked markers. Specifically, the concordance is considered significant when the observed concordance values for multiple markers in an interval agree with the predicted concordance values, as determined by a $\chi^2$ test (P. G. Hoel, *Introduction to Mathematical Statistics*. New York: John Wiley & Sons, 1971), incorporated by reference. To predict concordance at a nearby marker having recombination distance $\theta$ from the candidate marker, each individual with an affected/carrier parent is considered to be an independent Bernoulli trial for linkage. Since $(1-\theta)$ is the probability that the offspring remains linked at the nearby marker, with n as the total (unweighted IBS or weighted IBD) number of considered individuals, the binomial distribution provides the predicted concordance mean and variance parameters $$\mu = n * (1-\theta), \text{ and}$$

$$\sigma^2 = n * \theta * (1-\theta).$$

From these predicted distribution parameters, the $\chi^2$ test can be performed by evaluating a set of neighboring markers.

(5) A system for positionally cloning disease genes.

A system for positionally cloning a disease gene comprising the steps of:

1. Determining genotypes from STR loci using the method of FIG. 1B.
2. Entering data and pedigree information into a computer device with memory. This data entry can be done manually, or automatically, as in (D. K. Pathak and M. W. Perlin, "Intelligent Interpretation of PCR Products in 1D Gels for Automatic Molecular Diagnostics," in *Seventh Annual IEEE Symposium on Computer-based Medical Systems*, Winston-Salem, N.C., 1994), incorporated by reference.
3. Running a computer program such as LINKAGE to localize traits on the genetic map (G. M. Lathrop and J. -M. Lalouel, "Efficient computations in multilocus linkage analysis," *Amer. J. Hum. Genet.*, vol. 42, pp. 498–505, 1988), incorporated by reference.
4. Use an integrated genetic/physical map to positionally clone the disease gene using standard techniques (D. Cohen, I. Chumakov, and J. Weissenbach, *Nature*, vol. 366, pp. 698–701, 1993; B. -S. Kerem, J. M. Rommens, J. A. Buchanan, D. Markiewicz, T. K. Cox, A. Chakravarti, M. Buchwald, and L. -C. Tsui, "Identification of the cystic fibrosis gene: genetic analysis," *Science* vol. 245, pp. 1073–1080, 1989; J. R. Riordan, J. M. Rommens, B. -S. Kerem, N. Alon, R. Rozmahel, Z. Grzelczak, J. Zielenski, S. Lok, N. Plavsic, J. -L. Chou, M. L. Drumm, M. C. Iannuzzi, F. S. Collins, and L. -C. Tsui, "Identification of the cystic fibrosis gene: cloning and characterization of complementary DNA," *Science*, vol. 245, pp. 1066–1073, 1989), incorporated by reference.
5. Determine the sequence of the cloned gene.
6. Use the sequence of the cloned gene for diagnostic testing, for treating disease, and for developing pharmaceutical reagents.

(6) A system for genetically monitoring cancerous materials or other diseases.

A system for genetically monitoring cancerous materials or other diseases comprising the steps of:

1. Determining genotypes of cancerous tissues from STR loci using the method of FIG. 1B. In one preferred embodiment, the STRs are diagnostic tri- or tetranucleotide repeats associated with tumor progression and severity. In another preferred embodiment, the STRs are polynucleotide repeats used to quantitate the number chromosomal regions present in one sample, thereby determining chromosomal deletions and replicated chromosome regions.
2. Entering data and pedigree information into a computer device with memory. This data entry can be done manually, or automatically, as in (D. K. Pathak and M. W. Perlin, "Intelligent Interpretation of PCR Products in 1D Gels for Automatic Molecular Diagnostics," in *Seventh Annual IEEE Symposium on Computer-based Medical Systems*, Winston-Salem, N.C., 1994), incorporated by reference.
3. Evaluate the temporal course of the determined genotypes of tumors to facilitate accurate diagnosis, (Zhang, Y., Coyne, M. Y., Will, S. G., Levenson, C. H., and Kawasaki, E. S. (1991). Single-base mutational analysis of cancer and genetic diseases using membrane bound modified oligonucleotides. *Nucleic Acids Research*, 19(14):3929–33), incorporated by reference.

(7) A system for genetic fingerprinting.

A system for genetic fingerprinting comprising the steps of:

1. Determining genotypes of cancerous tissues from STR loci using the method of FIG. 1B.
2. Entering data and pedigree information into a computer device with memory. This data entry can be done manually, or automatically, as in (D. K. Pathak and M. W. Perlin, "Intelligent Interpretation of PCR Products in 1D Gels for Automatic Molecular Diagnostics," in *Seventh Annual IEEE Symposium on Computer-based Medical Systems*, Winston-Salem, N.C., 1994), incorporated by reference.

3. Storing, retrieving, comparing, and processing genetic STR-based fingerprints (Jeffreys, A. J., Brookfield, J. F. Y., and Semeonoff, R. 1985. Positive identification of an immigration test-case using human DNA fingerprints. *Nature*, 317: 818–819.), incorporated by reference.

(8) A system for performing population genotyping studies.

A system for performing population genotyping studies comprising the steps of:

1. Determining the genotypes of STR loci for samples containing multiple chromosomes from STR loci using the method of FIG. 1B. These samples are pooled DNAs from one or more individuals. Referring to FIG. 1B, the preferred embodiment includes step 5" for genotyping by matrix processing, preferably by least squares (e.g., SVD) combination of the stutter pattern matrix together with the sizing and concentration data.

2. Entering data and pedigree information into a computer device with memory. This data entry can be done manually, or automatically, as in (D. K. Pathak and M. W. Perlin, "Intelligent Interpretation of PCR Products in 1D Gels for Automatic Molecular Diagnostics," in *Seventh Annual IEEE Symposium on Computer-based Medical Systems*, Winston-Salem, N.C., 1994), incorporated by reference.

3. Performing further population-based analyses such as association or linkage (A. E. H. Emery, *Methodology in Medical Genetics: an introduction to statistical methods, Second Edition Edition*. Edinburgh: Churchill Livingstone, 1986; J. Ott, *Analysis of Human Genetic Linkage, Revised Edition*. Baltimore, Md.: The Johns Hopkins University Press, 1991), incorporated by reference, or newer techniques based on dense genotyping (E. Feingold, P. O. Brown, and D. Siegmund, "Gaussian Models for Genetic Linkage Analysis Using Complete High-Resolution Maps of Identity by Descent," *Am. J. Hum. Genet.*, vol. 53, pp. 234–252, 1993; D. E. Goldgar, "Multipoint analysis of human quantitative genetic variation," *Am. J. Hum. Genet.*, vol. 47, pp. 957–967, 1990; S. -W. Guo, "Computation of Identity-by-Descent Proportions Shared by Two Siblings," *Am. J. Hum. Genet.*, vol. 54, pp. 1104–1109, 1994; N. Risch, "Linkage strategies for genetically complex traits. In three parts," *Am. J. Hum. Genet.*, vol. 46, pp. 222–253, 1990; N. J. Schork, "Extended Multipoint Identity-by-Descent Analysis of Human Quantitative Traits: Efficiency, Power, and Modeling Considerations," *Am. J. Hum. Genet.*, vol 53, pp 1306–1319, 1993), incorporated by reference, to localize genetic patterns of inheritance on the genome in populations.

(9) A system for assessing genetic risk in individuals.

A system for assessing genetic risk comprising the steps of:

1. Determining the genotypes of STR loci for multiple related individuals from STR loci using the method of FIG. 1B.

2. Entering data and pedigree information into a computer device with memory. This data entry can be done manually, or automatically, as in (D. K. Pathak and M. W. Perlin, "Intelligent Interpretation of PCR Products in 1D Gels for Automatic Molecular Diagnostics," in *Seventh Annual IEEE Symposium on Computer-based Medical Systems*, Winston-Salem, N.C., 1994), incorporated by reference.

3. Using the genotypic information to assess risk in individuals for multigenic traits (E. Feingold, P. O. Brown, and D. Siegmund, "Gaussian Models for Genetic Linkage Analysis Using Complete High-Resolution Maps of Identity by Descent," *Am. J. Hum. Genet.*, vol. 53, pp. 234–252, 1993; D. E. Goldgar, "Multipoint analysis of human quantitative genetic variation," *Am. J. Hum. Genet.*, vol 47, pp. 957–967, 1990; S. -W. Guo, "Computation of Identity-by-Descent Proportions Shared by Two Siblings," *Am. J. Hum. Genet.*, vol. 54, pp. 1104–1109, 1994; N. Risch, "Linkage strategies for genetically complex traits. In three parts," *Am. J. Hum. Genet.*, vol. 46, pp. 222–253, 1990; N. J. Schork, "Extended Multipoint Identity-by-Descent Analysis of Human Quantitative Traits: Efficiency, Power, and Modeling Considerations," *Am. J. Hum. Genet.*, vol. 53, pp. 1306–1319, 1993), incorporated by reference. Performing further risk assessment using classical methods (A. E. H. Emery, *Methodology in Medical Genetics: an introduction to statistical methods, Second Edition Edition*. Edinburgh: Churchill Livingstone, 1986; A. E. H. Emery and D. L. Rimoin, ed., *Principles and practice of medical genetics*. Edinburgh: Churchill Livingstone, 1983; J. Ott, *Analysis of Human Genetic Linkage, Revised Edition*. Baltimore, Md.: The Johns Hopkins University Press, 1991; I. D. Young, *Introduction to Risk Calculation in Genetic Counselling*. Oxford: Oxford University Press, 1991), incorporated by reference, to assess genetic risk of multigenic traits in individuals or groups.

(10) A method for multiplexing genotyping data by means of stutter.

In the current art, genotype readouts are multiplexed in several dimensions. The readout windows for each genotype may be multiplexed by lane (x-axis), size region for alleles of predetermined size (y-axis), fluorescent label (z-axis), or hybridization probe (z-axis). The current art employs non-overlapping windows, with at most one marker represented in a given genotyping window, so that the analysis of the demultiplexed genotyping trace or image evaluates at most one marker per genotyping window. These partitionings (e.g., of lane, size, label, and probe) set the bandwidth of the multiplexed gel experiment. For example, a fluorescent multiplexed ABI gel experiment running over a 6–8 hour period can currently multiplex 300–600 markers per gel run; with ultrathin gels (e.g., capillary arrays or slabs), greater rates are attained.

The art can be improved by "stutter-based multiplexed genotyping": exploiting stutter patterns to increase the multiplexing bandwidth, hence increase the total number of genotypings per gel run. In this method, multiple markers are run within the same window, and the stutter patterns that are associated with each marker are used to demultiplex and determine which alleles are associated with which marker. With stutter-based multiplexing, multiple marker locations can be assayed without partitioning into size regions.

The method for stutter-based multiplexed genotyping is comprised of the steps:

(a) obtaining nucleic acid material from a genome;

(b) amplifying one or more locations of the material;

(c) assaying the amplified material based on size and concentration;

(d) converting the assayed amplified material into a first set of electrical signals corresponding to size and concentration of the amplified material at the locations; and (e) operating on the first set of electrical signals produced from the amplified material with a second set of electrical signals corresponding to response patterns of the locations to produce a third set of clean electrical signals corresponding to the size and multiplicities of the unamplified material on the genome at the locations.

This method for stutter-based multiplexed genotyping extends the genotyping method of claim 1 by means of a set of locations. A set of locations is selected for multiplexing wherein each location preferably has a distinct stutter pattern, though possibly overlapping allele size regions. For each location, a second set of electrical signals corresponding to a response pattern of the location is formed, and is preferably represented as a matrix. These sets are preferably combined into a collection of sets in a joint matrix representation. In step b, known concentrations of the PCR primers of the markers are preferably used. Preferably, more than one location is amplified. These amplifications may be done in combination, or be done separately and then combined prior to step c. In step c, the sizes of the amplified material correspond to possibly superimposed marker allele signals from different locations. In step e, the operation is preferably determining by means of the stutter patterns the best fit in a least squares sense between a feasible genotype and the observed data.

As an illustrative example of the steps of the method with just two locations, one first selects two markers a and b having possibly similar allele sizes, but having different stutter patterns, and then determines experimentally the two stutter matrices A and B associated with the markers a and b. In this simulation example, these distinct stutter matrices are A =
| 1.0000 | 0 | 0 | 0 | 0 |
| 0.5000 | 1.0000 | 0 | 0 | 0 |
| 0.2500 | 0.6000 | 1.0000 | 0 | 0 |
| 0.1250 | 0.3000 | 0.7000 | 1.0000 | 0 |
| 0 | 0.1500 | 0.3500 | 0.8000 | 1.0000 |
| 0 | 0 | 0.1600 | 0.4000 | 0.9000 |
| 0 | 0 | 0 | 0.2000 | 0.4500 |
| 0 | 0 | 0 | 0 | 0.2200 | and
B =
| 1.0000 | 0 | 0 | 0 | 0 |
| 0.9000 | 1.0000 | 0 | 0 | 0 |
| 0.8000 | 0.9000 | 1.0000 | 0 | 0 |
| 0.1000 | 0.8000 | 0.9000 | 1.0000 | 0 |
| 0 | 0.1000 | 0.8000 | 0.9000 | 1.0000 |
| 0 | 0 | 0.1000 | 0.8000 | 0.9000 |
| 0 | 0 | 0 | 0.1000 | 0.8000 |
| 0 | 0 | 0 | 0 | 0.1000 |

The illustrative matrices A and B are then used to form a coupled set of linear equations $z = Ax + By$. Suppose that an individual has their actual alleles for the (overlapping in allele sizes) markers a and b expressed as the respective vectors x0 and y0, $$x0 = <1\ 0\ 1\ 0\ 0>$$

and $$y0 = <1\ 0\ 0\ 1\ 0>.$$

Then (following steps a, b, c, and d) the measured signal from the superposition of an individual's alleles from these two markers corresponds to:

$$\begin{aligned} z0 &= Ax0 + By0 \\ &= <1.0\ 0.5\ 1.25\ 0.825\ 0.35\ 0.16\ 0.0\ 0.0> + \\ &\phantom{=}\ <1.0\ 0.9\ 0.8\ 1.10\ 0.90\ 0.80\ 0.1\ 0.0> \\ &= <2.0\ 1.4\ 2.05\ 1.925\ 1.25\ 0.96\ 0.1\ 0.0> \end{aligned}$$

Trying out (in step e) all feasible solutions $<x,y>$, where x and y are each integer valued column vectors each having a sum that preferably does not exceed 2, one selects the vector which has the minimum error between observed data and predicted genotypes, $$\text{norm}(z0-(Ax+By)).$$

The best fit occurs with the actual genotypes x0 and y0:

$$z0-(A<1\ 0\ 1\ 0\ 0>+B<1\ 0\ 0\ 1\ 0>),$$

which has norm=0.0. Note that incorrect genotype solutions give larger norm values, e.g., even a slightly incorrect genotype $$x1=<1\ 0\ 1\ 0\ 0>$$

$$y1=<1\ 0\ 1\ 0\ 0>$$

has a norm $$\text{norm}(z0-(A<1\ 0\ 1\ 0\ 0>+B<1\ 0\ 1\ 0\ 0>))=1.2329$$

with an error value larger than that of the correct solution. Performing a simulation with +/−10% noise added to the computed data vector z0, the minimum error was reached at the correct solution (with a value of 0.1626), and the range of error values for incorrect feasible vectors was [0.5596, 5.8261]. I.e., the method is robust and accurate.

Enumerating all combinations of candidate allele solutions, and determining each candidate's deviation from measured data, establishes the correct alleles for multiple markers. This is computationally tractable. For a polynucleotide repeat region with n candidate repeat sizes, the number of candidate diploid solutions is $n^2$. Since n is generally less than 20, this solution number is less than 400. With k-fold within-window multiplexing, the total number of integer candidate vectors to explore is $n^{2k}$. For example, with n=20 and k=3, this set has size 64,000,000. Such sets are amenable to direct enumerative search. Further, the search can be reduced considerably using integer programming techniques (Papadimitriou CH, Steiglitz K (1983) Combinatorial Optimization: Algorithms and Complexity. Prentice-Hall, Englewood Cliffs, N.J.), incorporated by reference. More efficient search enables a more marker locations to be included in the stutter-based multiplexing.

Herein, means or mechanism for language has been used. The presence of means is pursuant to 35 U.S.C. §112 paragraph and is subject thereto. The presence of mechanism is outside of 35 U.S.C. §112 and is not subject thereto.

Although the invention has been described in detail in the foregoing embodiments for the purpose of illustration, it is to be understood that such detail is solely for that purpose and that variations can be made therein by those skilled in the art without departing from the spirit and scope of the invention except as it may be described by the following claims.

What is claimed is:

1. A method for genotyping comprised of the steps:

(a) obtaining DNA or RNA material from a genome;

(b) amplifying locations of the material, with the length of the location not exceeding fifty kilobases and the location containing a polynucleotide repeat region;

(c) labelling the amplified material with labels;

(d) converting the labels with a sensing device which produces a first electrical signal;

(e) removing a reproducible pattern of the amplification from the first electrical signal to form a third electrical signal; and (f) producing from the third electrical signal a genotype of the material at the locations.

2. A method as described in claim 1 wherein the reproducible pattern of the amplification corresponds to a PCR stutter artifact of the location.

3. A method as described in claim 1 wherein the step of removing the reproducible pattern from the first electrical signal includes the step of a deconvolution procedure.

4. A method as described in claim 1 wherein the step of removing the reproducible pattern from the first electrical signal includes the step of deconvolving with a second electrical signal related to the reproducible pattern of the amplification.

5. A method as described in claim 1 wherein the step of removing the reproducible pattern includes the step of deconvolving with matrix processing of the electrical signals.

6. A method as described in claim 1 wherein the determination of the second set of electrical signals of the location is comprised of the steps:

(a) obtaining DNA or RNA material from a genome;

(b) amplifying locations of the material, with the length of the location not exceeding fifty kilobases and the location containing a polynucleotide repeat region;

(c) labelling the amplified material with labels;

(d) converting the labels with a sensing device which produces a first electrical signal; and (e) operating on the first set of electrical signals produced from the amplified material to produce a second set of electrical signals corresponding to reproducible patterns of the locations.

7. A method as described in claim 1 wherein the obtaining step pools DNA or RNA from one or more individuals.

8. A method as described in claim 1 wherein the amplifying step includes more than one polynucleotide repeat location.

9. A method as described in claim 1 wherein the amplifying step includes more than one polynucleotide repeat location, and the size properties of these locations may overlap.

10. A method as described in claim 1 wherein the amplifying step includes more than one polynucleotide repeat location, the size properties of these locations may overlap, and the reproducible patterns of the different locations include bands of the same size.

11. A method as described in claim 1 wherein the amplifying step includes more than one polynucleotide repeat location, the size properties of these locations may overlap, the reproducible patterns of the different locations include bands of the same size, and the reproducible patterns of the different locations are used in genotyping the locations.

12. A method as described in claim 1 wherein the removing step combines the first electrical signal with a second set of electrical signals corresponding to reproducible patterns of the locations.

13. A system for genotyping comprising:

(a) means for obtaining nucleic acid material from a genome;

(b) means for amplifying locations of the material, said amplifying means in communication with the nucleic acid material;

(c) means for assaying the amplified material based on size and concentration, said assaying means in communication with amplifying means;

(d) means for converting the assayed amplified material into a first set of electrical signals corresponding to size and concentration of the amplified material at the locations, said converting means in communication with the assaying means; and (e) means for removing a reproducible pattern of amplification from the first electrical signal with a second electrical signal to form a third electrical signal, said means in communication with the sets of electrical signals.

14. A system as described in claim 13 wherein:

(a) the amplifying means includes polymerase chain reaction, or harvesting cloned cells;

(b) the assaying means includes gel or ultrathin gel electrophoresis, or mass spectroscopy, or denaturing gradient gel electrophoresis, or differential hybridization, or sequencing by hybridization;

(c) the converting means employs labeling with detection including radioactivity, or fluorescence, or phosphorescence, or chemiluminescence, or visible light, or ions, or pH, or electricity, or resistivity, or biotinylation, or antibodies; and includes the detecting means which includes a photomultiplier tube; a radioactivity counter, a resistivity sensor, a pH meter, or an optical detector; and (d) the operating means includes statistical moment determinations, or Fourier transformation, or optimal filtering, or polynomial calculations, or matrix computations.

15. A method for analyzing genetic material of an organism comprising the steps of:

(a) obtaining DNA or RNA material from the organism;

(b) amplifying locations of the material, with the average length of the locations not exceeding fifty kilobases and each location including a polynucleotide repeat region;

(c) labelling the amplified material with labels;

(d) converting the labels with a sensing device which produces a first electrical signal; and (e) producing the genotype of an amplified location of the genetic material in an electronic acquisition system comprising a region having a radius of less than five feet at a rate exceeding 100 genotypes per hour.

16. A method as described in claim 1 wherein in the removing step there is the step of removing a plurality of reproducible patterns of the amplification.

* * * * *